(12) United States Patent
Taniguchi

(10) Patent No.: US 8,335,423 B2
(45) Date of Patent: Dec. 18, 2012

(54) IMAGE DISPLAY APPARATUS, IMAGE INTERPRETATION SUPPORT SYSTEM AND COMPUTER-READABLE RECORDING MEDIUM

(75) Inventor: Katsuyoshi Taniguchi, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 99 days.

(21) Appl. No.: 12/984,742

(22) Filed: Jan. 5, 2011

(65) Prior Publication Data

US 2011/0249952 A1 Oct. 13, 2011

Related U.S. Application Data

(63) Continuation of application No. PCT/JP2010/061186, filed on Jun. 30, 2010.

(30) Foreign Application Priority Data

Jul. 29, 2009 (JP) ................................. 2009-177033

(51) Int. Cl.
*H04N 5/775* (2006.01)
*H04N 9/80* (2006.01)

(52) U.S. Cl. ........................................ 386/230; 386/248

(58) Field of Classification Search .................. 386/230, 386/224, 248, 353, 239
See application file for complete search history.

(56) References Cited

U.S. PATENT DOCUMENTS 7,545,410 B2 * 6/2009 Oka et al. .................... 348/211.2
2006/0064321 A1 3/2006 Sasano et al.
2007/0083396 A1 * 4/2007 Kanada et al. .................... 705/3
2008/0039692 A1 2/2008 Hirakawa
2008/0172255 A1 7/2008 Hirakawa et al.
2008/0232702 A1 9/2008 Kimoto
2009/0027486 A1 1/2009 Hirakawa et al.

FOREIGN PATENT DOCUMENTS

| EP | 1 618 828 A1 | 1/2006 |
|---|---|---|
| EP | 1 918 870 A1 | 5/2008 |
| EP | 1 920 709 A1 | 5/2008 |
| JP | 200661278 A | 3/2006 |
| JP | 200775158 A | 3/2007 |
| JP | 2007143648 A | 6/2007 |
| JP | 2007260064 A | 10/2007 |
| JP | 200836028 A | 2/2008 |

OTHER PUBLICATIONS

European Supplementary Search Report dated Feb. 24, 2012 from corresponding European Patent Application No. EP 10 80 4222.7.
International Search Report dated Aug. 31, 2010 of corresponding International PCT Application No. PCT/JP2010/061186.

* cited by examiner

*Primary Examiner* — Robert Chevalier
(74) *Attorney, Agent, or Firm* — Scully, Scott, Murphy & Presser, P.C.

(57) ABSTRACT

An image display apparatus includes an image playback unit that plays a group of a series of images in chronological order; an operating unit that is used to input an operation when an image that is being played in the image playback unit is subjected to image interpretation; an image interpretation operation recording unit that records an operation content which is input from the operating unit in an order with respect to the image that is being played in the image playback unit; an image interpretation operation image creating unit that creates, using the operation content recorded in the image interpretation operation recording unit, a series of images according to the order; and an image interpretation operation image display unit that displays the image created by the image interpretation operation image creating unit.

18 Claims, 24 Drawing Sheets

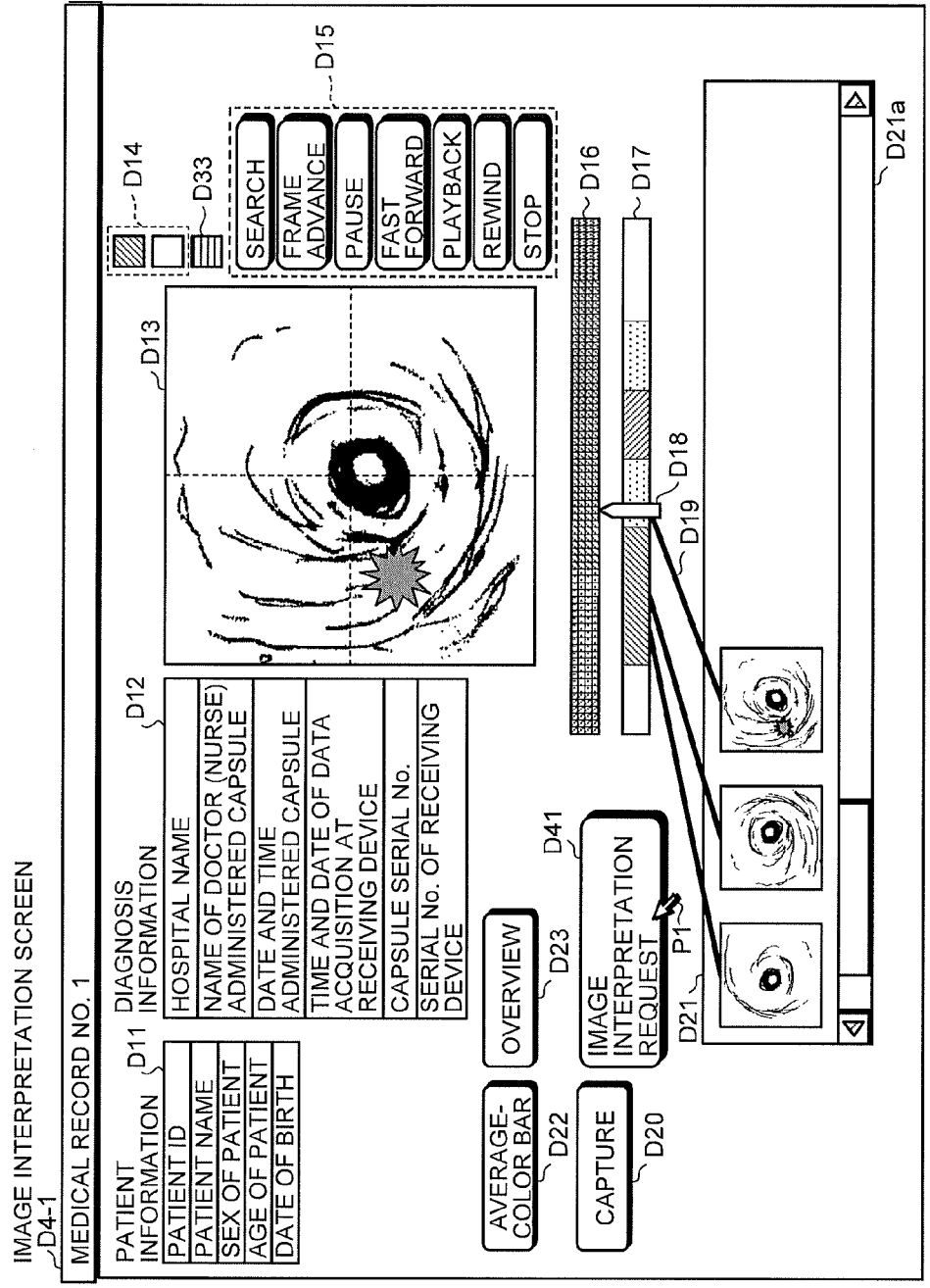

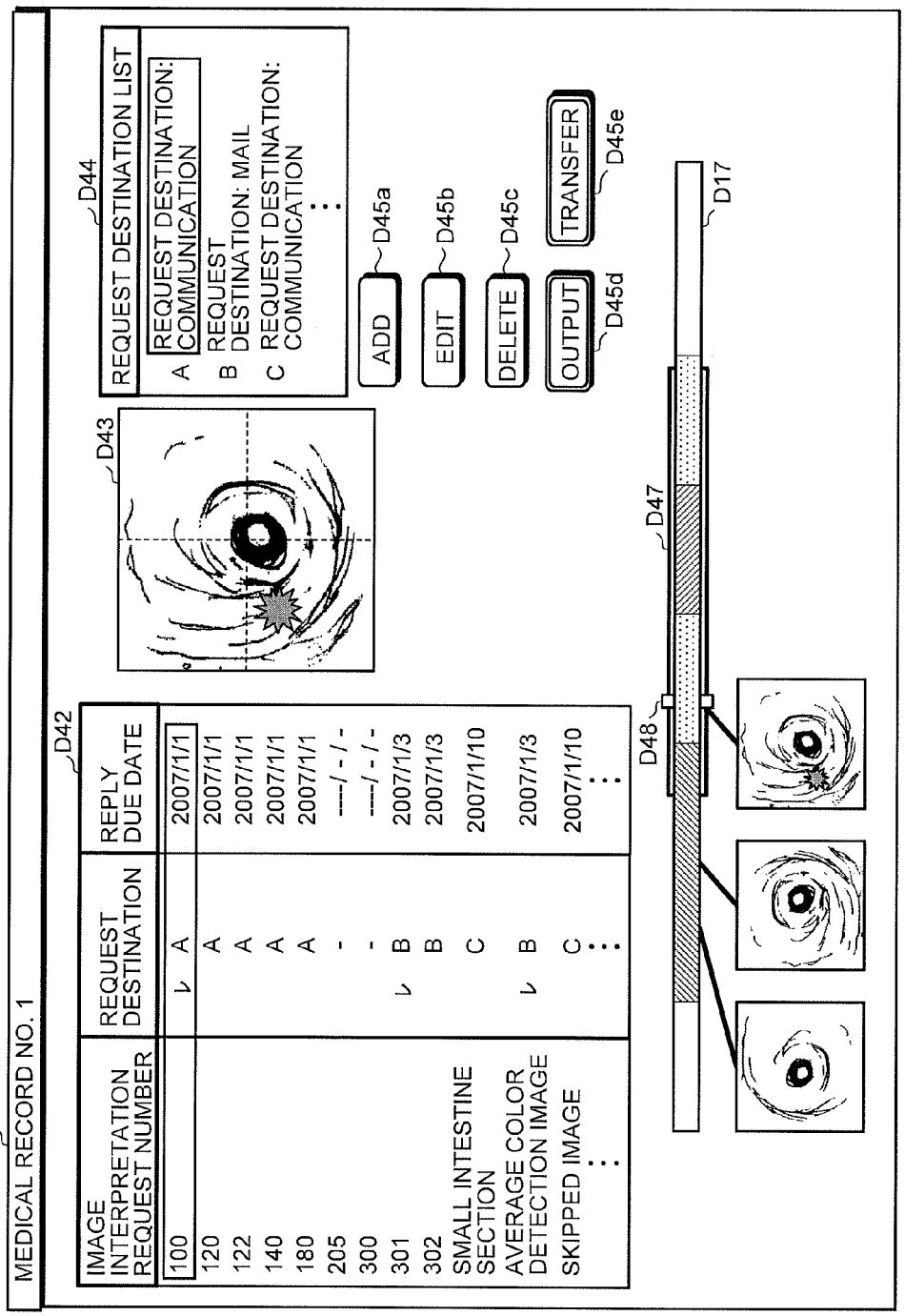

IMAGE DISPLAY APPARATUS, IMAGE INTERPRETATION SUPPORT SYSTEM AND COMPUTER-READABLE RECORDING MEDIUM

CROSS-REFERENCE TO RELATED APPLICATIONS

This application is a continuation of PCT international application Ser. No. PCT/JP2010/061186 filed on Jun. 30, 2010 which designates the United States, incorporated herein by reference, and which claims the benefit of priority from Japanese Patent Application No. 2009-177033, filed on Jul. 29, 2009, incorporated herein by reference.

BACKGROUND OF THE INVENTION

1. Field of the Invention

The present invention relates to image display apparatuses, image interpretation support systems, and computer-readable recording media, and more particularly, to an image display apparatus, an image interpretation support system, and a computer-readable recording medium that reproduce image interpretation performed, by an observer, on an image group obtained using a capsule endoscope that is introduced into a subject.

2. Description of the Related Art

When a subject is examined using a capsule endoscope that is introduced into a subject and that captures inside the subject, as disclosed in, for example, Japanese Laid-open Patent Publication No. 2007-143648, image groups acquired by a capsule endoscope are observed using a pseudo moving image list or a still image list, whereby an operation for selecting abnormalities is performed. This operation is called image interpretation. Because the number of image groups captured by the capsule endoscope is about as many as 60,000 (corresponding to about eight hours), it takes a lot of time to perform image interpretation the captured image groups, and moreover, it requires concentration.

For software (hereinafter, referred to as "image interpretation software") that is used to assist the operation of the image interpretation, various image interpretation support functions, such as a playback function including playback speed regulation, pause, and frame advance and an automatic extraction function of automatically extracting a red-dominated image, are prepared.

SUMMARY OF THE INVENTION

An image display apparatus according to an aspect of the present invention includes an image playback unit that plays a group of a series of images arranged in chronological order; an operating unit that is used to input an operation when an image that is being played in the image playback unit is subjected to image interpretation; an image interpretation operation recording unit that records an operation content that are input from the operating unit in an order with respect to the image that is being played in the image playback unit; an image interpretation operation image creating unit that creates, using the operation content recorded in the image interpretation operation recording unit, a series of images according to the order; and an image interpretation operation image display unit that displays the images created by the image interpretation operation image creating unit.

An image display apparatus according to another aspect of the present invention includes an image playback means for playing a group of a series of images arranged in chronological order; an operating means for inputting an operation when an image that is being played in the image playback means is subjected to image interpretation; an image interpretation operation recording means for recording an operation content that are input from the operating means in an order with respect to the image that is being played in the image playback means; an image interpretation operation image creating means for creating, using the operation content recorded in the image interpretation operation recording means, a series of images according to the order; and an image interpretation operation image display means for displaying the images created by the image interpretation operation image creating means.

An image interpretation support system according to still another aspect of the present invention includes an image display unit that includes an image playback unit for playing a group of a series of images arranged in chronological order; an operating unit for inputting an operation when an image that is being played in the image playback unit is subjected to image interpretation; an image interpretation operation recording unit for recording an operation content that are input from the operating unit in an order with respect to the image that is being played in the image playback unit; an image interpretation operation image creating unit for creating, using the operation content recorded in the image interpretation operation recording unit, a series of images according to the order; an image interpretation operation image display unit for displaying the images created by the image interpretation operation image creating unit; an image cutting unit for cutting out a part of the group of the series of images in the order; and an image interpretation request transmitting unit for transmitting, to a request destination via a network, an image interpretation request of the part of the group that is cut out by the image cutting unit; and a request destination information processing unit for receiving the image interpretation request from the image displaying unit.

An image interpretation support system according to still another aspect of the present invention includes an image display means that includes an image playback means for playing a group of a series of images arranged in chronological order; an operating means for inputting an operation when an image that is being played in the image playback means is subjected to image interpretation; an image interpretation operation recording means for recording an operation content that are input from the operating means in an order with respect to the image that is being played in the image playback means; an image interpretation operation image creating means for creating, using the operation content recorded in the image interpretation operation recording means, a series of images according to the order; an image interpretation operation image display means for displaying the images created by the image interpretation operation image creating means; an image cutting means for cutting out a part of the group of the series of images in the order; and an image interpretation request transmitting means for transmitting, to a request destination via a network, an image interpretation request of the part of the group that is cut out by the image cutting means; and a request destination information processing means for receiving the image interpretation request from the image displaying means.

A computer-readable recording medium according to still another aspect of the present invention has stored therein an image interpretation support program including instructions for supporting image interpretation of a group of a series of images in chronological order. The image interpretation support program causes a computer to execute: an image play process step of playing the group of the series of images; an image interpretation monitoring process step of monitoring an operation that is input when an image that is being played is subjected to image interpretation; an image interpretation operation recording process step of recording an operation content in an order, obtained at the image interpretation operation recording process with respect to the image that is being played; an image interpretation operation image creating process step of creating a series of images in accordance with the order using the operation content recorded at the image interpretation operation recording process; and an image interpretation operation image display process step of displaying the image created at the image interpretation operation image creating process.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 23 is a schematic diagram illustrating an example of an image interpretation screen of an image display apparatus according to a fourth embodiment of the present invention; and FIG. 24 is a schematic diagram illustrating an example of an image interpretation request screen of the image display apparatus according to the fourth embodiment of the present invention.

DETAILED DESCRIPTION OF THE PREFERRED EMBODIMENTS

Figure 1:
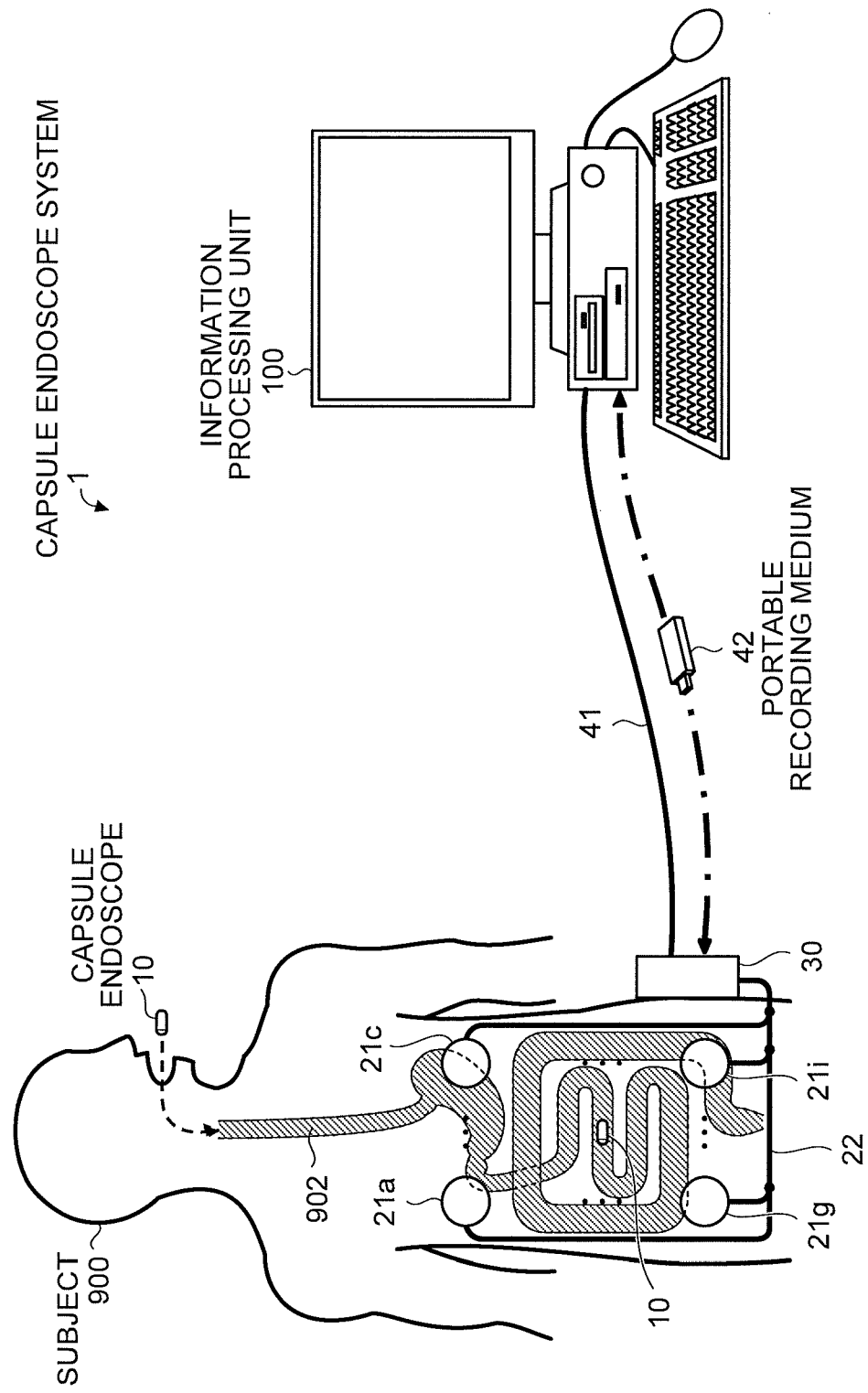
FIG. 1 is a schematic diagram illustrating, in outline, the configuration of a capsule endoscope system that includes an image display apparatus according to a first embodiment of the present invention.

In the following, preferred embodiments of the present invention will be described in detail with reference to the accompanying drawings. However, the present invention is not limited to the embodiment. In the drawings used for the following description, shapes, sizes, and positional relationships are only schematically illustrated so that the content of the present invention can be understood. Accordingly, the present invention is not limited to only the shapes, the sizes, and the positional relationships illustrated in the drawings.

First Embodiment

In the following, the configuration and the operation of a capsule endoscope system that includes an image display apparatus according to a first embodiment of the present invention will be described in detail with reference to the drawings. In the first embodiment, as a body-insertable apparatus, a capsule endoscope that is orally introduced into a subject and that acquires in-vivo images inside the subject while moving through the esophagus to the anus of the subject is used as an example; however, the present invention is not limited thereto. Various types of body-insertable apparatus can be used; for example, a capsule endoscope that captures in-vivo images inside the subject while remaining at various organs, such as the stomach or the intestine, of the subject can also be used.

Configuration

FIG. 1 is a schematic diagram illustrating, in outline, the configuration of a capsule endoscope system 1 that includes an image display apparatus according to the first embodiment of the present invention. As illustrated in FIG. 1, the capsule endoscope system 1 includes a capsule endoscope 10 whose size is such that it can be swallowed by a subject 900; a receiving device 30 that can receive an image signal transmitted from the capsule endoscope 10 as a wireless signal; and an information processing unit 100 that can input/output data to/from the receiving device 30 via a wired or wireless communication interface 41, such as a universal serial bus (USB) interface or Bluetooth, or via a portable recording medium 42, such as a flash memory (registered trademark). The receiving device 30 and the information processing unit 100 are external devices for the capsule endoscope system 1. The information processing unit 100 corresponds to the image display apparatus according to the first embodiment of the present invention.

External antennas 21a to 21i (hereinafter, reference numeral 21 denotes a given external antenna) are connected to the receiving device 30 via a connection cable 22 or a balun (not shown). A wireless signal that is output from the capsule endoscope 10 is input to the receiving device 30 via the external antenna 21.

The capsule endoscope 10 periodically acquires, for example, in-vivo images and sequentially transmits the acquired in-vivo images to the receiving device 30. The receiving device 30 stores, in the portable recording medium 42 as needed, the in-vivo images received from the capsule endoscope 10 or transmits them to the information processing unit 100 via the communication interface 41. Furthermore, the in-vivo images stored in the portable recording medium 42 are input to the information processing unit 100 from the portable recording medium 42 later.

The information processing unit 100 is an information processing unit, such as a workstation or a personal computer, that includes a display unit, such as a monitor. The information processing unit 100 displays, to an image interpreter, a part or the entire input in-vivo image using image interpretation software, which will be described later. By using the image interpretation software, the image interpreter performs image interpretation on the in-vivo image that is displayed, on the information processing unit 100, as a pseudo moving image or a still image, whereby diagnosing, for example, the condition of the subject 900.

Figure 2:
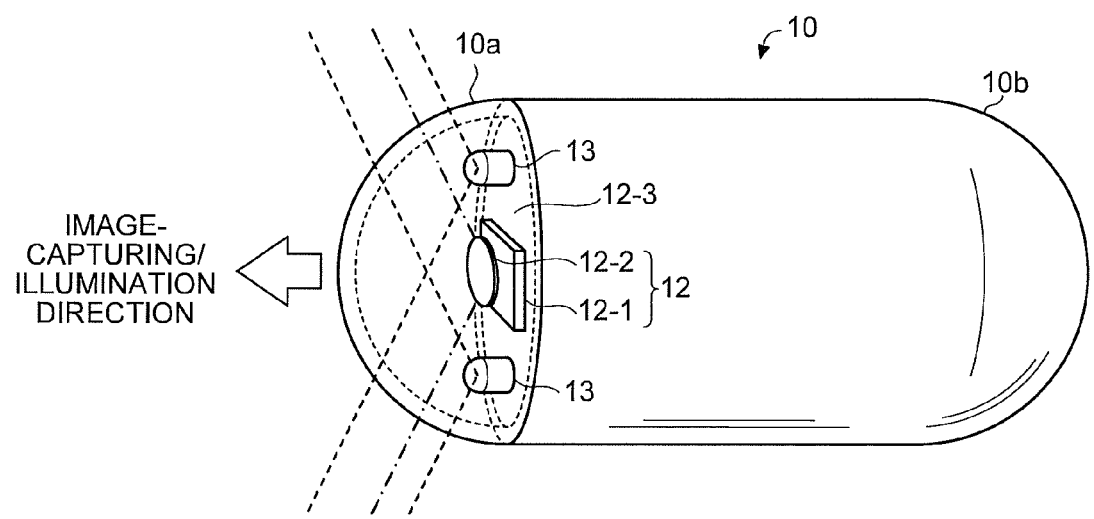
FIG. 2 is a schematic diagram illustrating, in outline, the configuration of a capsule endoscope according to the first embodiment of the present invention.

FIG. 2 is a schematic diagram illustrating, in outline, the configuration of the capsule endoscope 10 according to the first embodiment of the present invention. As illustrated in FIG. 2, the capsule endoscope 10 is constituted of a capsule-shaped container (casing) that has a substantially cylindrical or semi-ellipsoidal container 10b with one end thereof being hemispherical, i.e., in a dome-shape, and the other end thereof being opened and that has a hemispherical optical dome 10a that is fitted into an opening of the container 10b, whereby inside the container 10b is sealed in a liquid-tight manner. The container 10b mainly forms one end of the body portion of the capsule-shaped container (10a, 10b), whereas the optical dome 10a forms the other end of the capsule-shaped container (10a, 10b). The size of this capsule-shaped container (10a, 10b) is such that it can be swallowed by, for example, the subject 900. In the first embodiment of the present invention, the optical dome 10a is formed of at least transparent material.

Furthermore, the capsule endoscope 10 includes an imaging unit 12 functioning as image capturing means for capturing an image inside the subject 900 and also includes an illumination unit 13 functioning as illuminating means for illuminating inside the subject 900 when an image is captured. The imaging unit 12 includes an image-capturing device 12-1, such as a CCD camera or a CMOS camera, that creates image data of an in-vivo image in accordance with, for example, an optical image formed on a light-receiving surface and also includes an optical system 12-2 including, for example, an objective lens arranged on the light-receiving surface side of the image-capturing device 12-1. Both the image-capturing device 12-1 and the optical system 12-2 are mounted on a circuit substrate 12-3 that includes, for example, a driving circuit that is used to drive them.

On the circuit substrate 12-3, the illumination unit 13 constituted of, for example, a light emitting diode (LED) that emit light into the subject 900 at the time of image capturing and the driving circuit of thereof are mounted. By being operated under the control of a signal processing unit 11, which will be described later, the driving circuit of the illumination unit 13 periodically creates an image signal of an in-vivo image (for example, 2 frames per second) and inputs it to the signal processing unit 11, which will be described later. In the description below, the imaging unit 12 and the illumination unit 13 is assumed to include driving circuits, respectively.

The circuit substrate 12-3 on which the imaging unit 12 and the illumination unit 13 are mounted is arranged on the optical dome 10a side in the capsule-shaped container (10a, 10b) in such a manner that the light-receiving surface of the image-capturing device 12-1 and the light emitting direction of the illumination unit 13 faces towards the subject 900 via the optical dome 10a. Accordingly, as illustrated in FIG. 2, the image-capturing direction of the imaging unit 12 and the illumination direction of the illumination unit 13 are oriented towards the outside of the capsule endoscope 10 via the optical dome 10a. With this configuration, it is possible to captured images inside the subject 900 using the imaging unit 12 while illuminating, using the illumination unit 13, inside the subject 900.

In the first embodiment of the present invention, it has been mentioned that the capsule endoscope 10 that includes a set of the imaging unit 12 and the illumination unit 13 is used as an example; however, the present invention is not limited thereto. For example, it is also possible to use a pantoscopic capsule endoscope that includes a plurality of sets of imaging unit and illumination unit. For example, a binocular capsule endoscope has a hollow cylindrical shape container, corresponding to the body portion thereof, that accommodates components of the capsule endoscope and that has openings at their ends, into which transparent optical domes are fitted. Furthermore, at each opening, an imaging unit and an illumination unit are arranged such that they are oriented towards the outside of the capsule endoscope via the optical domes, respectively.

Figure 3:
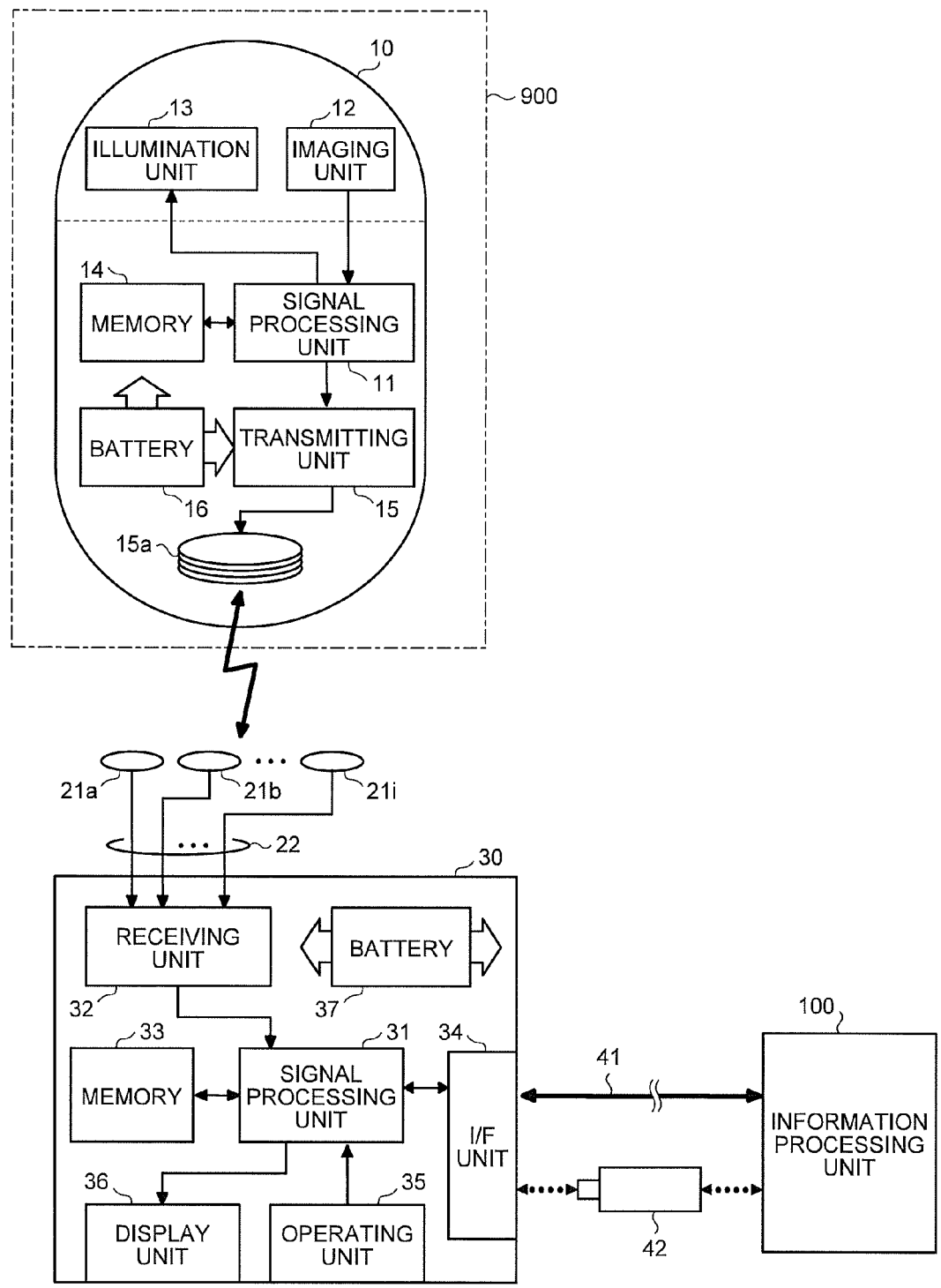
FIG. 3 is a block diagram illustrating, in outline, the configuration of the capsule endoscope and a receiving device according to the first embodiment of the present invention.

In the following, the outline of the internal configuration of the capsule endoscope 10 and the receiving device 30 according to the first embodiment will be described with reference to FIG. 3. FIG. 3 is a block diagram illustrating, in outline, the configuration of the capsule endoscope 10 and the receiving device 30 according to the first embodiment of the present invention.

As illustrated in FIG. 3, the capsule endoscope 10 includes the imaging unit 12 that captures images inside the subject 900 to acquire in-vivo images; the illumination unit 13 that illuminates inside the subject 900 when an image is captured; the signal processing unit 11 that controls each unit in the capsule endoscope 10 and performs predetermined image processing on an image signal of an in-vivo image read from the imaging unit 12; a memory 14 that temporarily stores therein a control program of various operations performed by the signal processing unit 11 and temporarily stores therein image data of the in-vivo image subjected to the predetermined image processing in the signal processing unit 11; a transmitting unit 15 and an antenna 15a that transmit, outside as a wireless signal, the in-vivo image subjected to the predetermined image processing in the signal processing unit 11; and a battery 16 that supplies electrical power to each unit in the capsule endoscope 10. The battery 16 is supposed to include a power circuit that boosts the electrical power supplied from a primary battery or a secondary battery, such as a button battery.

As illustrated in FIG. 3, the receiving device 30 includes a receiving unit 32 that receives, via the external antenna 21, the in-vivo image that is wirelessly transmitted from the capsule endoscope 10; a signal processing unit 31 that controls each unit in the receiving device 30 and performs predetermined image processing on image data of the in-vivo image received by the receiving unit 32; a memory 33 that temporarily stores therein a control program of various operations performed by the signal processing unit 31 and temporarily stores therein image data of the in-vivo image subjected to the predetermined image processing in the signal processing unit 31; an I/F unit 34 that inputs, to the information processing unit 100 via the communication interface 41, a subject's image subjected to the predetermined image processing in the signal processing unit 31 or that stores the image in the portable recording medium 42; an operating unit 35 that receives various operation instructions or settings, from a user, with respect to the receiving device 30; a display unit 36 that notifies a user of various information or displays it to a user; and a battery 37 that supplies electrical power to each unit in the receiving device 30.

Figure 4:
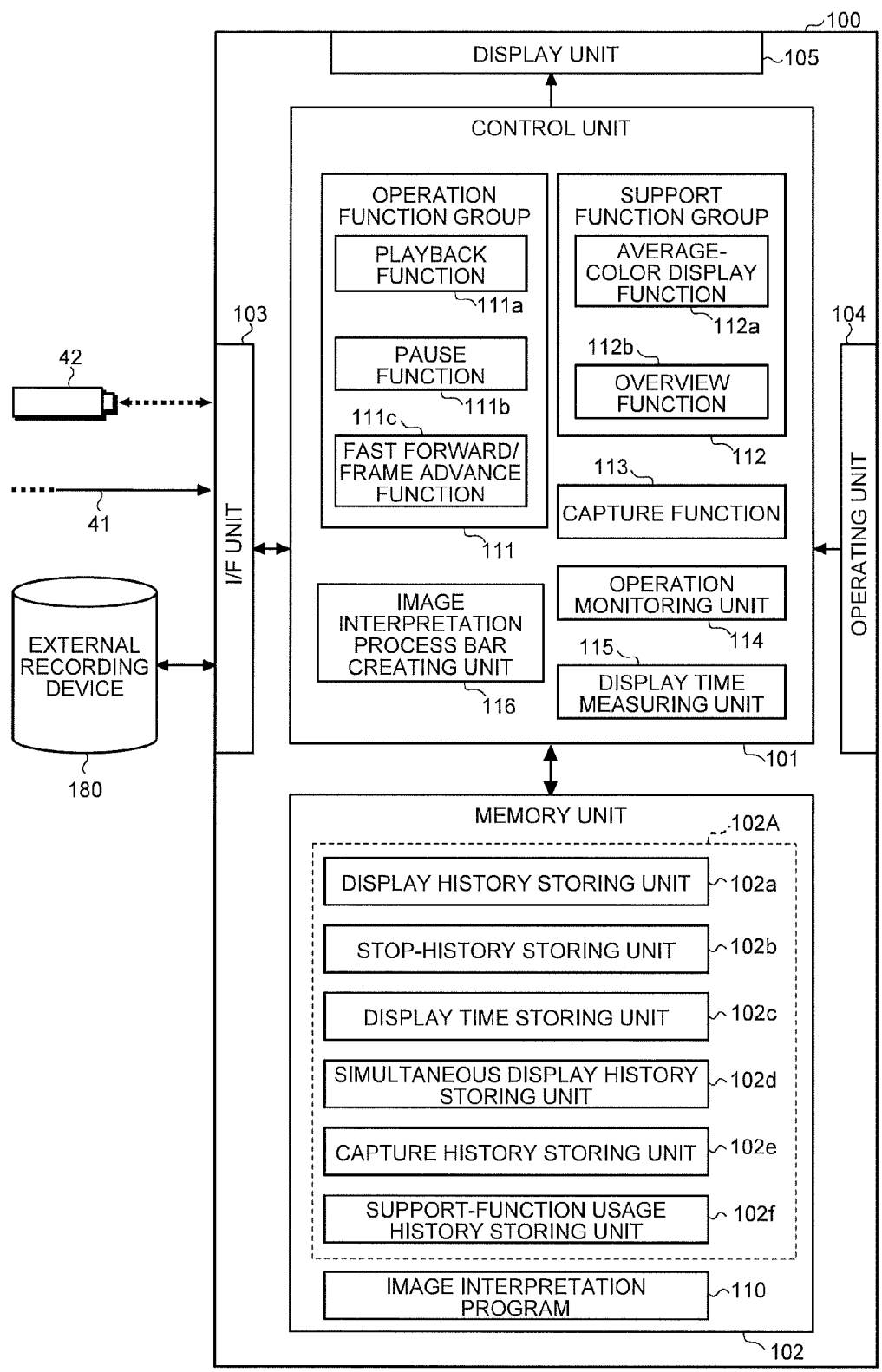
FIG. 4 is a block diagram illustrating, in outline, the configuration of an information processing unit corresponding to an image display apparatus according to the first embodiment of the present invention.

In the following, the information processing unit 100 that displays, using image interpretation software which will be described later, image data of an in-vivo image received from the receiving device 30 to a user and that provides a support function of image interpretation will be described in detail with reference to the drawings. FIG. 4 is a block diagram illustrating, in outline, the configuration of the information processing unit 100 corresponding to the image display apparatus according to the first embodiment of the present invention.

As illustrated in FIG. 4, the information processing unit 100 includes an I/F unit 103 that is used to input image data of an in-vivo image via the communication interface 41 or the portable recording medium 42; a control unit 101 that provides a user with an image interpretation environment of image data received from the I/F unit 103 and that controls each unit in the information processing unit 100; a memory unit 102 that stores therein various programs and setting information performed by the control unit 101 and that stores therein the image data received from the I/F unit 103 or various information created by the control unit 101; an operating unit 104 that receives, from a user, image interpretation or other operations; and a display unit 105 that displays an image interpretation screen or another screen that is used for a user to perform image interpretation of the in-vivo image. Furthermore, the information processing unit 100 can also include an external recording device 180 or an internal recording device that is used to accumulate received in-vivo images. It is possible to use various kinds of recording media, such as a USB memory, a hard disk drive (HDD), a magneto-optic disk (MO), a CD-R, or a DVD-R, for the portable recording medium 42.

With the above configuration, both the control unit 101 and the display unit 105 function as an image playback unit that plays back a group of in-vivo images in chronological order. The operating unit 104 functions as an operating unit that is used to input an operation when an image that is being played back in the image playback unit is subjected to image interpretation. An operation monitoring unit 114 and a display time measuring unit 115 in the control unit 101 and the memory unit 102 function as an image interpretation operation recording unit that records image interpretation operation data, which is received from the operating unit 104, with respect to an image that is being played in the image playback unit while maintaining the ordering. An image interpretation process bar creating unit 116 in the control unit 101 functions as an image interpretation operation image creating unit that creates, using the image interpretation operation data recorded in the image interpretation operation recording unit, an image interpretation process bar D17 (see FIG. 5) that corresponds to a series of operation images arranged in the ordering. The control unit 101 and the display unit 105 also function as an image interpretation operation image display unit that displays an image created by the image interpretation operation image creating unit.

With the above configuration, the control unit 101 reads, for example, an image interpretation program 110 functioning as an image interpretation support program stored in the memory unit 102 and executes it. By doing so, as a function that provides a user to perform image interpretation on a series of in-vivo images that are received via the I/F unit 103, the following functions are implemented in the control unit 101: an operation function group 111 for, for example, a playback operation of an in-vivo image; a support function group 112 for supporting image interpretation performed on an in-vivo image that is being displayed on the display unit 105; and a capture function 113 of capturing the in-vivo image that is being displayed as an image of interest. Furthermore, the following units are implemented in the control unit 101 that executes the image interpretation program 110: the operation monitoring unit 114 that monitors various operations that is input by a user using the operating unit 104; the display time measuring unit 115 that measures the total display time of an in-vivo image that is being displayed on the display unit 105; and the image interpretation process bar creating unit 116 that creates an image interpretation process bar D17 in accordance with various operation contents (hereinafter, referred to as an "image interpretation operation data") that is obtained by the operation monitoring unit 114 or the display time measuring unit 115 and is stored in the memory unit 102. A series of in-vivo images (hereinafter, in some cases, referred to as an "in-vivo image group") mentioned here means a set of multiple in-vivo images of the subject 900 acquired, in chronological order, by the capsule endoscope 10 in a single observation.

The operation function group 111 includes, for example, a playback function 111a, a pause function 111b, and a fast forward/frame advance function 111c. The playback function 111a is a function of continuously playing back an in-vivo image group on the display unit 105 (pseudo moving image play). The pause function 111b is a function of pausing the continuous play and displaying, without interruption, the in-vivo image that is being displayed at the time of pausing. The fast forward/frame advance function 111c is a function of increasing or decreasing a playback speed of the in-vivo image group.

The support function group 112 includes, for example, an average-color display function 112a and an overview function 112b. The average-color display function 112a is a function of extracting, in chronological order, color information on a group of in-vivo images, creating strip-shaped images (average-color bar) along the time axis in accordance with the extracted color information, and displaying the created average-color bar as a graphical user interface (GUI) on the display unit 105. The overview function 112b is a function of reducing or thinning out all or a part of the group of in-vivo images and displaying them on the display unit 105. In addition to the average-color display function 112a and the overview function 112b described above, the support function group 112 can also include, for example, an express view function, an automatic speed regulation function, and a normal display function.

Figure 5:
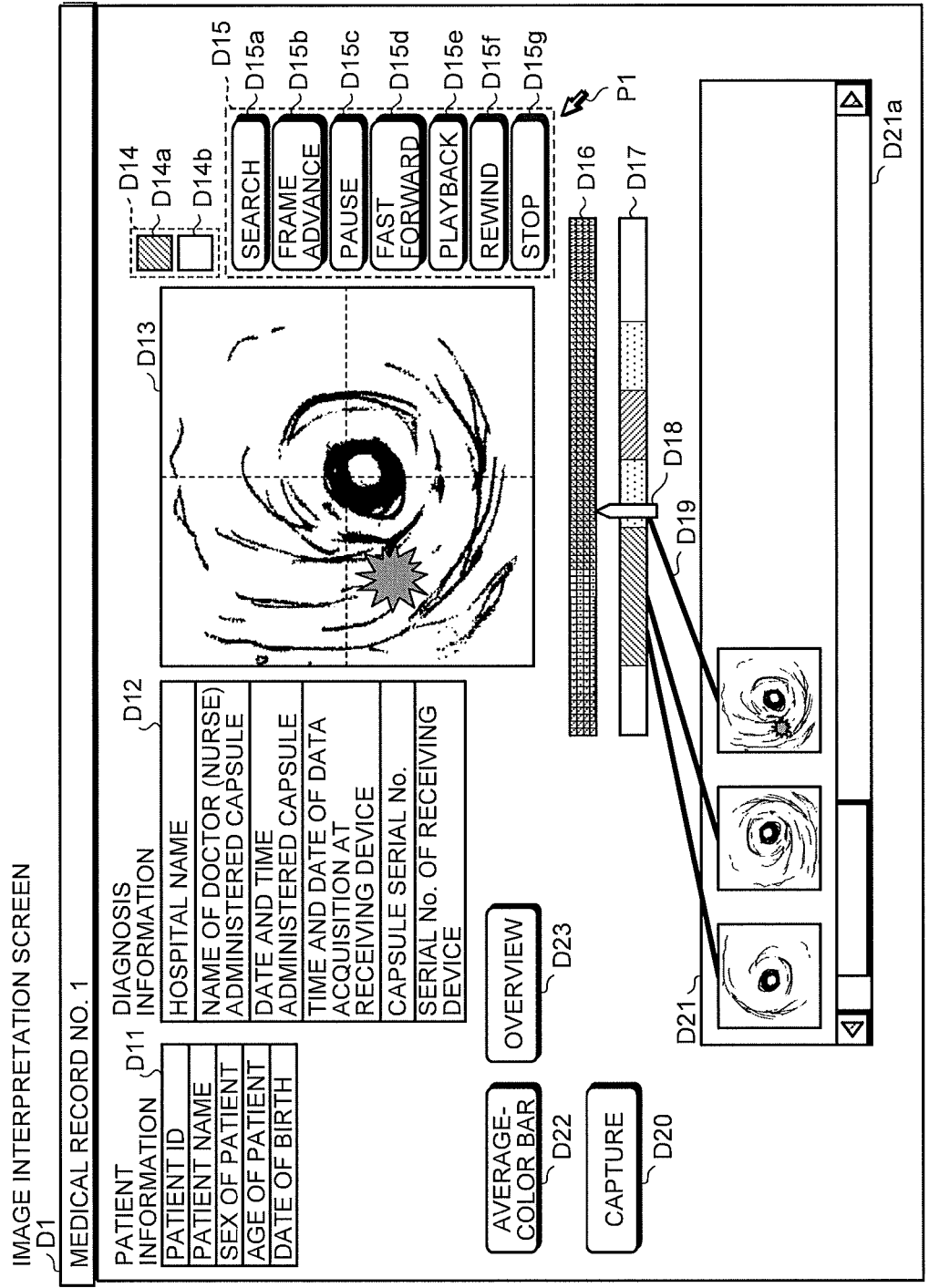
FIG. 5 is a schematic diagram illustrating an example of an image interpretation screen according to the first embodiment of the present invention.

In the following, an image interpretation GUI screen (hereinafter, referred to as an "image interpretation screen"), which is displayed on the display unit 105 by the image interpretation program 110 executed by the control unit 101, will be described in detail with reference to the drawings. In addition, the image interpretation program 110 executed by the control unit 101 will also be described in detail. FIG. 5 is a schematic diagram illustrating an example of an image interpretation screen according to the first embodiment of the present invention.

As illustrated in FIG. 5, an image interpretation screen D1 includes a patient information D11 that is used to identify the subject 900 corresponding to a patient; examination information D12 that is used to identify an examination performed on the subject 900; a main display area D13 where a group of in-vivo images is played; and an image interpretation information display unit D14 that displays information on the previous or current image interpretation with respect to the in-vivo image that is being displayed on the main display area D13. Furthermore, the image interpretation screen D1 also includes a playback operation button group D15 with which a user controls the playing of an in-vivo image in the main display area D13; an average-color bar D16 created in accordance with the group of in-vivo images; an image interpretation process bar D17 that displays the process of image interpretation currently or previously performed on the group of in-vivo images; and a slider D18 that can move on the image interpretation process bar D17 along the average-color bar D16. Furthermore, the image interpretation screen D1 also includes a capture button D20 that receives, from a user, an instruction to capture the in-vivo image that is being displayed in the main display area D13; a captured image display area D21 that displays, as a list, captured in-vivo images, thumbnail images thereof, reduced images, or thinned out images; and a leader line D19 that connects the image displayed in the captured image display area D21 to the position of the target image on the image interpretation process bar D17.

The image interpretation information display unit D14 includes, for example, an already-interpreted-image indication mark D14a and a support-function use status indication mark D14b. The already-interpreted-image indication mark D14a displays whether the in-vivo image that is being displayed in the main display area D13 has been previously subjected to image interpretation one or more times. Accordingly, by viewing the already-interpreted-image indication mark D14a, a user can check whether the in-vivo image that is being displayed in the main display area D13 has been previously subjected to image interpretation. Furthermore, each piece of information indicated by the already-interpreted-image indication mark D14a and the support-function use status indication mark D14b can be represented by a color or a pattern, or can be represented by a text or a pointer P1. Furthermore, for example, by changing the color of the already-interpreted-image indication mark D14a in accordance with the display time during which a target in-vivo image is displayed using a pause function when it is previously subjected to image interpretation, it is possible for a user to check the degree of attention of that in-vivo image.

The support-function use status indication mark D14b displays the use status of an image interpretation support function with respect to the previous image interpretation performed on the in-vivo image that is being displayed in the main display area D13. Accordingly, for example, by changing the color of the support-function use status indication mark D14b in accordance with the image interpretation support function that is used at the time of image interpretation, it is possible for a user to visually check the image interpretation support function that is used when the in-vivo image is subjected to image interpretation.

The playback operation button group D15 is a group of buttons that is used to control the playing of the in-vivo image in the main display area D13 in accordance with an instruction received from a user to the operation function group 111 that is implemented by the image interpretation program 110 executed by the control unit 101. The playback operation button group D15 includes, for example, a search button D15a, a frame advance button D15b, a pause button D15c, a fast forward button D15d, a playback button D15e, a rewind button D15f, and a stop button D15g.

The search button D15a is a button that is used for a user to input an instruction to return an in-vivo image to be played in the main display area D13 to the top image in a group of in-vivo images. For example, if a user operates a pointer P1 on the display unit 105 using the operating unit 104 and clicks the search button D15a, the control unit 101 calls, for example, the playback function 111a and allows the playback function 111a to play again the group of in-vivo images from the top image in the main display area D13.

The frame advance button D15b or the fast forward button D15d is a button that is used for a user to input an instruction to increase or decrease the playback speed of the group of in-vivo images in the main display area D13 greater or lower than the normal playback speed. For example, if a user operates the pointer P1 and clicks the frame advance button D15b or the fast forward button D15d, the control unit 101 calls, for example, the fast forward/frame advance function 111c and allows the fast forward/frame advance function 111c to increase or decrease the playback speed in the main display area D13 greater or lower than the normal playback speed. Furthermore, if a user clicks the frame advance button D15b or the fast forward button D15d, it is also possible to configure the button such that a predetermined speed can be increased or decreased in accordance with the number of click times. In such a case, the playback speed of the in-vivo image in the main display area D13 can be changed gradually, thus allowing a user to perform image interpretation more effectively.

The pause button D15c is a button that is used for a user to input an instruction to pause the continuous playback of the group of in-vivo images in the main display area D13. for example, if a user operates the pointer P1 and clicks the pause button D15c, the control unit 101 calls, for example, the pause function 111b and allows the pause function 111b to pause playback in the main display area D13 and to display, in the main display area D13, the in-vivo image that was displayed just before the pause in the main display area D13. To restart the playback, for example, a user clicks again the pause button D15c using the pointer P1.

The playback button D15e is a button that is used for a user to input an instruction to start playback of the group of in-vivo images in the main display area D13. For example, if a user operates the pointer P1 and clicks the playback button D15e, the control unit 101 calls, for example, the playback function 111a and allows the playback function 111a to start continuous playback of a group of in-vivo images in the main display area D13. Furthermore, for example, if reverse playback, which will be described below, is performed, the control unit 101 switches the playback of the in-vivo images, from reverse playback to forward playback, that is performed by the playback function 111a. The forward playback mentioned here means playback performed in chronological order.

The rewind button D15f is a button that is used for a user to input an instruction to play back, in the main display area D13, a group of in-vivo images in reverse chronological order, i.e., reverse playback. For example, if a user clicks the rewind button D15f using the pointer P1, the control unit 101 calls, for example, the playback function 111a and allows the playback function 111a to start continuous reverse playback of a group of in-vivo images in the main display area D13.

The stop button D15g is a button that is used for a user to input an instruction to stop playback of the in-vivo image in the main display area D13. For example, if a user clicks the stop button D15g using the pointer P1, the control unit 101 calls, for example, the playback function 111a and allows the playback function 111a to stop playback/reverse playback that is currently performed.

On the average-color bar D16, color information extracted in chronological order from the group of in-vivo images is converted into strip-shaped images aligned along the time axis. Accordingly, by viewing the average-color bar D16, a user can check how a red portion of each subject image taken in chronological order is changed in the whole group of subject images or changed throughout inside the subject 900 along a lumen 902 (see FIG. 1). For example, the average-color bar D16 can be configured such that, if the average-color bar button D22 on the image interpretation screen D1 is clicked, the average-color bar D16 is embedded in the image interpretation screen D1. In such a case, if a user operates the pointer P1 using the operating unit 104 and clicks the average-color bar button D22, the control unit 101 calls, for example, the average-color display function 112a from the support function group 112 and allows the average-color display function 112a to create images displayed on the average-color bar D16 with respect to the group of subject images. Then, the control unit 101 embeds the created average-color bar D16 in a predetermined area on the image interpretation screen D1. Accordingly, the image interpretation screen D1 in which the average-color bar D16 is embedded is displayed on the display unit 105.

As described above, the image interpretation process bar D17 converts a process of image interpretation currently or previously performed on the group of in-vivo images into images of the group of in-vivo images aligned in chronological order and displays them. For example, if the current or the previous image interpretation time taken by a image interpreter with respect to each in-vivo image or the image interpretation speed is imaged and displayed on the image interpretation process bar D17, by viewing the image interpretation process bar D17, a user can check which part of the whole group of in-vivo images or throughout inside the subject 900 along the lumen 902 is carefully observed by the current or previous image interpreter, i.e., is subjected to image interpretation for a long time. However, the display of the image interpretation process bar D17 is not limited to the time taken by the image interpreter with respect to each in-vivo image. The image interpretation process bar D17 can also display imaged information, in chronological order, on an image interpretation operation performed by an image interpreter, such as a playback mode or the frame rate, or availability of a pause operation or of overview display with respect to each in-vivo image.

The image interpretation process bar D17 can be created as follows: image interpretation operation data is obtained by the operation monitoring unit 114 or the display time measuring unit 115, is stored in the memory unit 102, is read by the image interpretation process bar creating unit 116, and is imaged in chronological order. Furthermore, the created image interpretation process bar D17 is embedded in a predetermined area on the image interpretation screen D1 by the control unit 101 and is displayed on the display unit 105.

To create the image interpretation process bar D17 in the image interpretation process bar creating unit 116, the image interpretation operation data obtained by the operation monitoring unit 114 includes display history information indicating the number of times each in-vivo image is displayed in the main display area D13; stop-history information indicating the number of times the pause button D15c is clicked by a user during displaying of each in-vivo image in the main display area D13; simultaneous display history information indicating the number of in-vivo images that is simultaneously displayed, using the overview function 112b, at the time of image interpretation of each in-vivo image; capture history information indicating the number of times each in-vivo image is captured at the time of image interpretation; and support-function usage history information indicating the history of the image interpretation support function that is used at the time of image interpretation of each in-vivo image. Furthermore, the image interpretation operation data obtained by the display time measuring unit 115 includes display time information indicating the total display time during which each in-vivo image is displayed in the main display area D13. The capture history information can be information indicating whether an in-vivo image is simply captured or information indicating the number of times an in-vivo image is captured regardless of whether the in-vivo image is excluded from a target in-vivo image to be captured or is deleted.

If the average-color bar D16 is displayed together with the image interpretation process bar D17, both time axes thereof are preferably linked. By doing so, a user can easily check the depth of red or the red area in which an image interpreter carefully observes during the image interpretation. Furthermore, in addition to the average-color bar D16, for another bar, such as a time bar, that is created by imaging various kinds of information along the time axis, if such a bar is displayed together with the image interpretation process bar D17, both time axes thereof are preferably linked.

The captured image display area D21 displays, in chronological order as a list, in-vivo images or thumbnail images thereof that are instructed to be captured by a user (hereinafter, simply referred to as "captured images"). The thumbnail images can be reduced images or thinned-out images to be captured. In the captured image display area D21, it is also possible to arrange a slider D21a in such a manner that a display region can be slidable using the slider D21a.

For example, if a user operates the pointer P1 using the operating unit 104 and clicks the capture button D20 on the image interpretation screen D1, the control unit 101 calls the capture function 113. The capture function 113 specifies the in-vivo image displayed in the main display area D13 when the capture button D20 is clicked, the capture function 113 adds, to image data, a flag for identifying the in-vivo image as a captured image or stores that image data in a storing area that is additionally allocated in the memory unit 102. In this way, captured images are registered. The capture function 113 obtains or creates the in-vivo images registered as captured images or thumbnail images thereof and displays them along the captured image display area D21 in chronological order.

In addition to the above, the image interpretation screen D1 includes, for example, an overview button D23. If a user clicks the overview button D23 using, for example, the pointer P1, the control unit 101 calls, for example, the overview function 112b from the support function group 112. The overview function 112b reads, from the external recording device 180, for example, the group of in-vivo images or the whole or a part of the reduced or thinned-out images of the group of in-vivo images; creates an overview screen that is used to display the images, in chronological order in a list, in thumbnail view, or in express view; and displays the created overview screen on the display unit 105. By browsing the overview screen, a user can simultaneously check or compare multiple in-vivo images.

The image interpretation operation data, such as the display history information, the stop-history information, the display time information, the simultaneous display history information, the capture history information, and the support-function usage history information, is stored in, for example, an image interpretation operation data storage area 102A (see FIG. 4) in the memory unit 102 that includes a display history storing unit 102a, a stop-history storing unit 102b, a display time storing unit 102c, a simultaneous display history storing unit 102d, a capture history storing unit 102e, and a support-function usage history storing unit 102f; is read by the control unit 101 as needed; and is used for, for example, creating the image interpretation process bar D17.

Figure 6A:
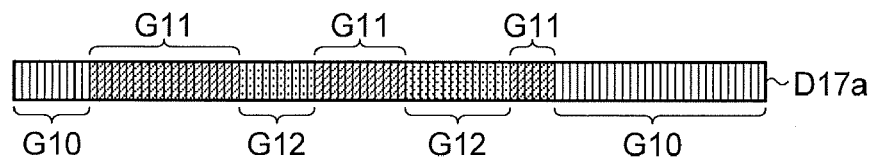
FIG. 6A is a schematic diagram illustrating an example of an image interpretation process bar that is created in accordance with image interpretation operation data that indicates whether each in-vivo image according to the first embodiment of the present invention has been previously subjected to image interpretation.
Figure 6B:
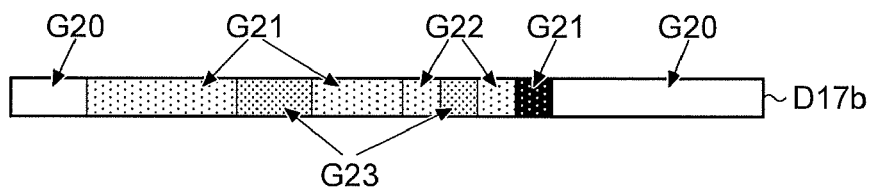
FIG. 6B is a schematic diagram illustrating an example of an image interpretation process bar that is created in accordance with the display time of previous image interpretation of each in-vivo image according to the first embodiment of the present invention.
Figure 6C:
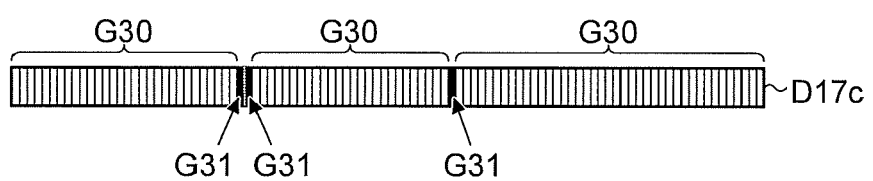
FIG. 6C is a schematic diagram illustrating an example of an image interpretation process bar that is created in accordance with image interpretation operation data that indicates whether each in-vivo image according to the first embodiment of the present invention is captured by the previous image interpretation.
Figure 6D:
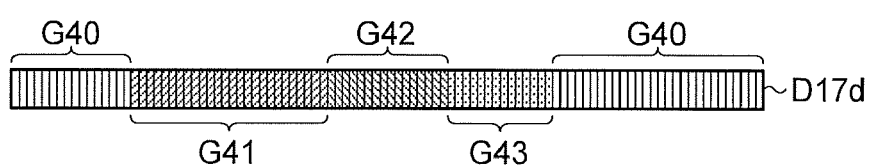
FIG. 6D is a schematic diagram illustrating an example of an image interpretation process bar that is created in accordance with the type of image interpretation support function that is used by the previous image interpretation of each in-vivo image according to the first embodiment of the present invention.
Figure 7:
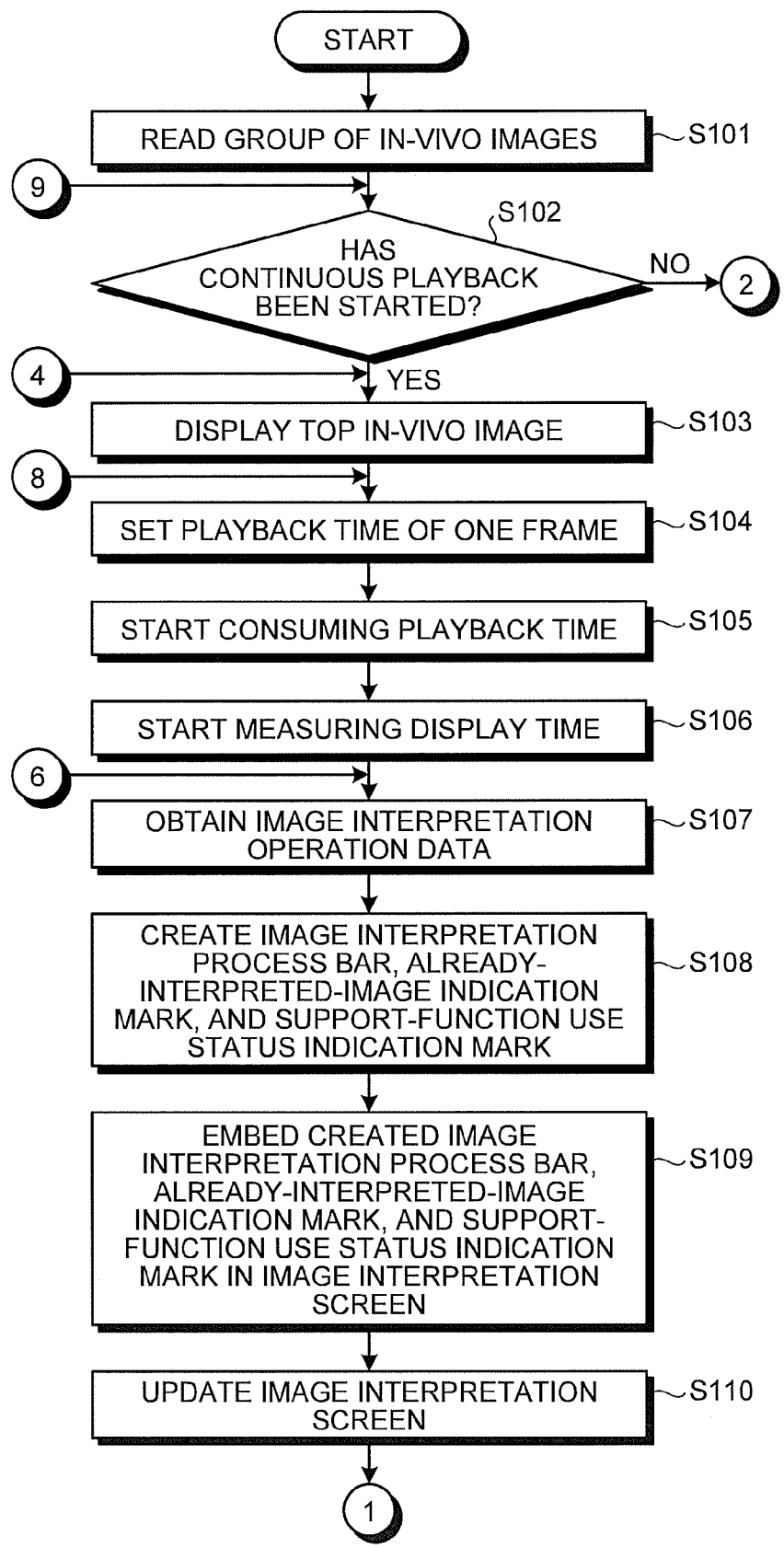
FIG. 7 is a flowchart illustrating a part of the flow of a method of confirming an image interpretation process according to the first embodiment of the present invention.
Figure 8:
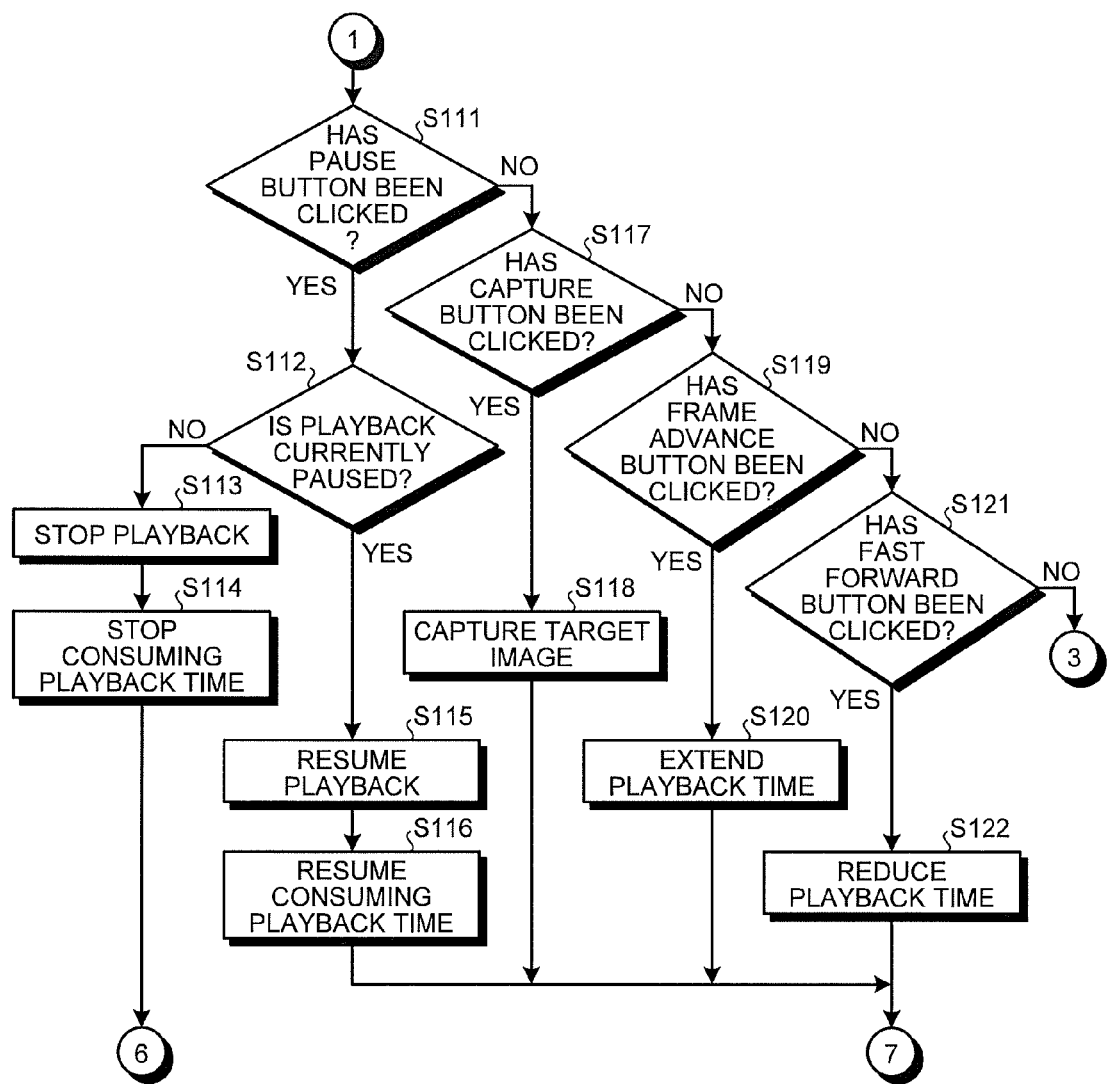
FIG. 8 is a flowchart illustrating another part of the flow of the method of confirming the image interpretation process according to the first embodiment of the present invention.

In the following, an example of the image interpretation process bar D17 created by the image interpretation process bar creating unit 116 in the first embodiment of the present invention will be described in detail with reference to the drawings. FIG. 6A is a schematic diagram illustrating an example of an image interpretation process bar that is created on an image interpretation screen of an information processing unit and is created in accordance with image interpretation operation data that indicates whether each in-vivo image according to the first embodiment of the present invention has been previously subjected to image interpretation. FIG. 6B is a schematic diagram illustrating an example of an image interpretation process bar that is created on the image interpretation screen of the information processing unit and is created in accordance with the display time of previous image interpretation of each in-vivo image according to the first embodiment of the present invention. FIG. 6C is a schematic diagram illustrating an example of an image interpretation process bar that is created on the image interpretation screen of the information processing unit and is created in accordance with image interpretation operation data that indicates whether each in-vivo image according to the first embodiment of the present invention is captured by the previous image interpretation. FIG. 6D is a schematic diagram illustrating an example of an image interpretation process bar that is created on the image interpretation screen of the information processing unit and is created in accordance with the type of image interpretation support function that is used by the previous image interpretation of each in-vivo image according to the first embodiment of the present invention.

As illustrated in FIG. 6A, the image interpretation process bar D17a, which is created in accordance with image interpretation operation data that indicates whether each in-vivo image has been previously subjected to image interpretation, displays each area associated with each in-vivo image aligned in chronological order in such a manner that each in-vivo image is color coded in accordance with the number of times image interpretation is performed. At this time, a more highlighted color is used for an area corresponding to an in-vivo image that is more frequently subjected to image interpretation. For example, an area G10 corresponding to an in-vivo image that has not yet been subjected to image interpretation is represented in a quiet color, such as white. An area G11 corresponding to an in-vivo image that has previously been image interpretation once is represented in a relatively pale color, such as blue. An area G12 corresponding to an in-vivo image that has previously been image interpretation twice is represented in deep color, such as blue, that is deeper than the color in the area G11. Accordingly, a user can easily and visually recognize a portion of the in-vivo images aligned in chronological order or a portion on the path inside the subject 900 that is carefully observed by an image interpreter in the previous image interpretation.

The image interpretation operation data indicating whether each in-vivo image has previously been subjected to image interpretation is stored in, for example, the display history storing unit 102a in the memory unit 102. Accordingly, the image interpretation process bar creating unit 116 creates the image interpretation process bar D17a in accordance with both the image interpretation operation data that is read by the display history storing unit 102a and the alignment of the group of in-vivo images in chronological order.

As illustrated in FIG. 6B, the image interpretation process bar D17b created in accordance with the display time of the previous image interpretation of each in-vivo image displays each area associated with each in-vivo image aligned in chronological order in such a manner that each in-vivo image is color coded in accordance with the total display time of each in-vivo image. At this time, a more highlighted color is used for an area corresponding to an in-vivo image that is displayed for a longer time. For example, an area G20 corresponding to an in-vivo image that has not yet been displayed is represented in a quiet color, such as white. An area G21 corresponding to an in-vivo image that is displayed for less than 10 seconds in total is represented in a relatively pale color, such as light green. An area G22 corresponding to an in-vivo image that is displayed for 10 seconds or more but less than one minute in total is represented in a deeper color than that in the area G21, such as green. An area G23 corresponding to an in-vivo image that is displayed for one minute or more in total is represented in further deeper color than that in the area G22, such as dark green. Accordingly, a user can easily and visually recognize a portion of the in-vivo images aligned in chronological order or a portion on the path inside the subject 900 that is carefully observed by an image interpreter in the previous image interpretation. The display time of each in-vivo image corresponds to a playback speed of pseudo moving image play of a group of in-vivo images. Accordingly, if the image interpretation process bar D17 is defined to be the display time of the previous image interpretation of each in-vivo image, the image interpretation process bar D17b can be alternatively used as a time bar indicating the position, on the time axis, of in-vivo image that is being displayed in the main display area D13.

Furthermore, the display time of the previous image interpretation of each in-vivo image is stored in, for example, the display time storing unit 102c in the memory unit 102 as part of the image interpretation operation data. Accordingly, the image interpretation process bar creating unit 116 creates the image interpretation process bar D17b in accordance with both the display time that is read by the display time storing unit 102c and the alignment of the group of in-vivo images in chronological order.

As illustrated in FIG. 6C, the image interpretation process bar D17c created in accordance with image interpretation operation data indicating whether each in-vivo image is captured in the previous image interpretation displays each area associated with each in-vivo image aligned in chronological order in such a manner that each in-vivo image is color coded depending on whether the status of the in-vivo image has been previously captured once. For example, an area G30 corresponding to an in-vivo image that has not previously been captured once is represented in a quiet color, such as white. An area G31 corresponding to an in-vivo image that has previously been captured once is represented in a color that can obtain sufficient contrast with respect to the area G30, such as black. Accordingly, a user can easily and visually recognize a portion of the in-vivo images aligned in chronological order or a portion on the path inside the subject 900 that is carefully observed by an image interpreter in the previous image interpretation.

The image interpretation operation data indicating whether each in-vivo image has been captured in the previous image interpretation is stored in, for example, the capture history storing unit 102e in the memory unit 102. Accordingly, the image interpretation process bar creating unit 116 creates the image interpretation process bar D17c in accordance with both the image interpretation operation data that is read by the capture history storing unit 102e and alignment of the group of in-vivo images in chronological order.

As illustrated in FIG. 6D, image interpretation process bar D17d created in accordance with the type of image interpretation support function that is used in the previous image interpretation of each in-vivo image displays each area associated with each in-vivo image aligned in chronological order in such a manner that each in-vivo image is color coded in accordance with an image interpretation support function, such as the average-color display function 112a or the overview function 112b, that is used when image interpretation is performed. At this time, the image interpretation process bar D17d is color coded in accordance with the type of image interpretation support function that is used. Furthermore, a more highlighted color is used for an area corresponding to an in-vivo image in which a greater number of types of the image interpretation support function is used. For example, an area G40 corresponding to an in-vivo image in which the image interpretation support function has not been used in the previous image interpretation is represented in a quiet color, such as white. An area G41 corresponding to an in-vivo image in which the image interpretation support function that is used in the previous image interpretation is the average-color display function 112a is represented in a relatively pale color, such as vermilion. An area G42 corresponding to an in-vivo image in which an image interpretation support function that is used in the previous image interpretation is the overview function 112b is represented in a relatively pale color, such as yellow, and represented in a color different from that used in the area G41. An area G43 corresponding to an in-vivo image in which the image interpretation support functions that are used in the previous image interpretation are both the average-color display function 112a and the overview function 112b is represented in a more highlighted color than that is used in the areas G41 and G42, such as purple. Accordingly, a user can easily and visually recognize a portion of the in-vivo images aligned in chronological order or a portion on the path inside the subject 900 that is carefully observed, i.e., that is subjected to image interpretation using a greater number of image interpretation support functions, by an image interpreter in the previous image interpretation. The type of image interpretation support function that is used in the previous image interpretation is stored in, for example memory, the display time storing unit 102c in the memory unit 102 as part of the image interpretation operation data.

Regarding the image interpretation process bars D17a to D17d illustrated in FIGS. 6A to 6D, the difference in image interpretation operation data is represented in a color; however the present invention is not limited thereto. For example, they can be represented using the type or the brightness of the texture to be mapped in an area or represented using a combination thereof. Furthermore, two or more combinations of the above examples can be used for the display of the image interpretation process bar D17. Furthermore, the shape of the image interpretation process bar D17 is not limited to a bar shape. Various modifications are possible so long as an image interpretation process can be visually represented, such as a graph.

Operation

In the following, the operation of confirming an image interpretation process implemented in the information processing unit 100 according to the first embodiment of the present invention will be described with reference to the drawings. FIGS. 7 to 10 are flowcharts illustrating the flow of a method of confirming an image interpretation process according to the first embodiment of the present invention. In the following, a description will be given by focusing on the operation of the control unit 101 that implements the operation of confirming the image interpretation process by executing the image interpretation program 110.

As illustrated in FIGS. 7 to 10, if the control unit 101 reads and executes the image interpretation program 110 that is stored, for example, in the memory unit 102 and starts the operation of confirming the image interpretation process, the control unit 101, first, reads image data of a group of in-vivo images from the external recording device 180 via the I/F unit 103 (Step S101). By executing the image interpretation program 110, functions like that illustrated in FIG. 4 are implemented in the control unit 101.

Then, the control unit 101 monitors whether a user clicks the playback button D15e via the operating unit 104 using the pointer P1 (Step S102). If the result of the determination at Step S102 is that the playback button D15e is clicked (Yes at Step S102), the control unit 101 calls the playback function 111a in the operation function group 111 and allows the playback function 111*a* to display, on the display unit 105, the top image of the group of in-vivo images (Step S103: an image playback process).

Furthermore, the control unit 101 sets the display time of each in-vivo image, i.e., a time that is set as the playback time of one frame, in a timer (not shown) (Step S104). Subsequently, the control unit 101 starts consuming the playback time that is set (Step S105) and measures, using the display time measuring unit 115, the total display time of the in-vivo image that is being displayed on the display unit 105 (Step S106). At Step S104, if the playback time is set to an initial value, for example, three seconds, the control unit 101 sets the initial value as a playback time for one frame. If the playback time is extended or reduced at Step S120 or S122, which will be described later, the control unit 101 sets the extended or reduced time as the playback time for one frame. At Step S106, if the target in-vivo image is displayed for, for example, the second time, the display time measuring unit 115 measures a second display time by adding a first display time thereto.

Then, the control unit 101 obtains image interpretation operation data that is stored in the memory unit 102 by the operation monitoring unit 114 and the display time measuring unit 115 (Step S107) and creates, in accordance with the obtained image interpretation operation data, the image interpretation process bar D17, the already-interpreted-image indication mark D14*a*, and the support-function use status indication mark D14*b* (Step S108: an image interpretation operation image creation process). Furthermore, the control unit 101 embeds, in the image interpretation screen D1, the created image interpretation process bar D17, the created already-interpreted-image indication mark D14*a*, and the created support-function use status indication mark D14*b* (Step S109) and updates, using the embedded image interpretation screen D1, the image interpretation screen D1 that is being displayed on the display unit 105 (Step S110: an image interpretation operation image display process). The operation monitoring unit 114 and the display time measuring unit 115 always monitor the operation content that is input from the operating unit 104 to the image interpretation screen D1 or measure the display time of each subject image and store the display time in a predetermined area in the memory unit 102 (an image interpretation monitoring process and an image interpretation operation recording process).

The image interpretation operation data that is read from the memory unit 102 by the control unit 101 at Step S107 can be the image interpretation operation data that is obtained by the operation monitoring unit 114 and the display time measuring unit 115 in the previous image interpretation and is stored in the memory unit 102 or the image interpretation operation data that is obtained by the operation monitoring unit 114 and the display time measuring unit 115 in the image interpretation that is currently being performed and is stored in the memory unit 102. If the image interpretation operation data is the one obtained in the previous image interpretation, the image interpretation process bar D17 indicating the previous image interpretation process in chronological order is displayed on the image interpretation screen D1. In such a case, it is possible to learn, from the image interpretation process bar D17, the previous image interpretation performed by an image interpreter. In addition, it is also possible to perform image interpretation focusing on an in-vivo image that is carefully observed in the previous image interpretation or an in-vivo image that is not carefully observed in the previous image interpretation. If the image interpretation operation data is the one obtained in the image interpretation that is currently being performed, the image interpretation process bar D17 that indicates, in chronological order, the image interpretation process from the beginning to the current is displayed on the image interpretation screen D1. In such a case, when image interpretation is performed by going back to the previous in-vivo image, it is possible to easily specify the in-vivo image that is carefully observed by an image interpretation.

Furthermore, the image interpretation operation data that is read from the memory unit 102 by the control unit 101 at Step S107 can be both the image interpretation operation data of the previous image interpretation and the image interpretation operation data of the image interpretation that is currently being performed. In this case, it is possible to configure the image interpretation process bar creating unit 116 in such a manner that image interpretation process bar D17 created using the image interpretation operation data of the previous image interpretation is updated, in substantially real time, using newly obtained image interpretation operation data of image interpretation that is currently being performed.

Then, the control unit 101 determines whether a user selects, using the pointer P1 using the operating unit 104, any one of buttons in the playback operation button group D15. For example, the control unit 101, first, determines whether a user clicks the pause button D15*c* using the pointer P1 (Step S111). If the result of the determination at Step S111 is that the pause button D15*c* is clicked (Yes at Step S111), the control unit 101 then determines whether the playback in the display unit 105 is currently paused (Step S112). If the playback is not paused (No at Step S112), the control unit 101 stops, using the pause function 111*b*, the playback of the group of in-vivo images on the display unit 105 (Step S113) and stops consuming the playback time that is measured using a timer (not shown) (Step S114). Thereafter, the control unit 101 returns to Step S107. The timer still continues measuring the display time even when the playback of the in-vivo images stops on the display unit 105.

In contrast, if the result of the determination at Step S112 is that the playback is paused (Yes at Step S112), the control unit 101 resumes, using the pause function 111*b*, the playback of the in-vivo images that is stopped (Step S115) and also resumes consuming the playback time that is set (Step S116). Then, the control unit 101 moves to Step S132 in FIG. 9.

Furthermore, if the result of the determination at Step S111 is that the pause button D15*c* is not clicked (No at Step S111), the control unit 101 then determines whether a user clicks the capture button D20 using the pointer P1 (Step S117). If the capture button D20 is clicked (Yes at Step S117), the control unit 101 captures, using the capture function 113, image data of the in-vivo image that is being displayed on the display unit 105 (Step S118) and then move to Step S132 in FIG. 9.

Furthermore, if the result of the determination at Step S117 is that the capture button D20 is not clicked (No at Step S117), the control unit 101 then determines whether a user clicks the frame advance button D15*b* using the pointer P1 (Step S119). If the frame advance button D15*b* is clicked (Yes at Step S119), by using the fast forward/frame advance function 111*c*, the control unit 101 extends the playback time of one frame that is currently set by a predetermined time, for example, five seconds (Step S120). For example, if an initial value of a time that is set as the playback time of one frame is three seconds and a time that is to be extended is 5 seconds, the extended time that is set as the playback time of one frame becomes eight seconds. Then, the control unit 101 moves to Step S132 in FIG. 9. Furthermore, for example, the playback time can be configured such that, by setting an upper limit value, for example, 60 seconds, to the playback time, the playback time does not exceed that upper limit value.

In contrast, if the result of the determination at Step S119 is that the frame advance button D15b is not clicked (No at Step S119), the control unit 101 then determines whether a user clicks the fast forward button D15d using the pointer P1 (Step S121). If the fast forward button D15d is clicked (Yes at Step S121), the control unit 101 reduces, using the fast forward/frame advance function 111c, the playback time of one frame that is currently set by a predetermined time, for example, five seconds (Step S122). For example, if a time that is set as the playback time of one frame is 18 seconds and a time to be reduced is five seconds, the reduced time that is set as the playback time of one frame becomes 13 seconds. Then, the control unit 101 moves to Step S132 in FIG. 9. Furthermore, for example, the playback time is configured such that, by setting a lower limit value for example, 0.5 seconds, to the playback time, if the reduced playback time becomes equal to or lower than the lower limit value, the lower limit value is automatically set as the playback time.

Figure 9:
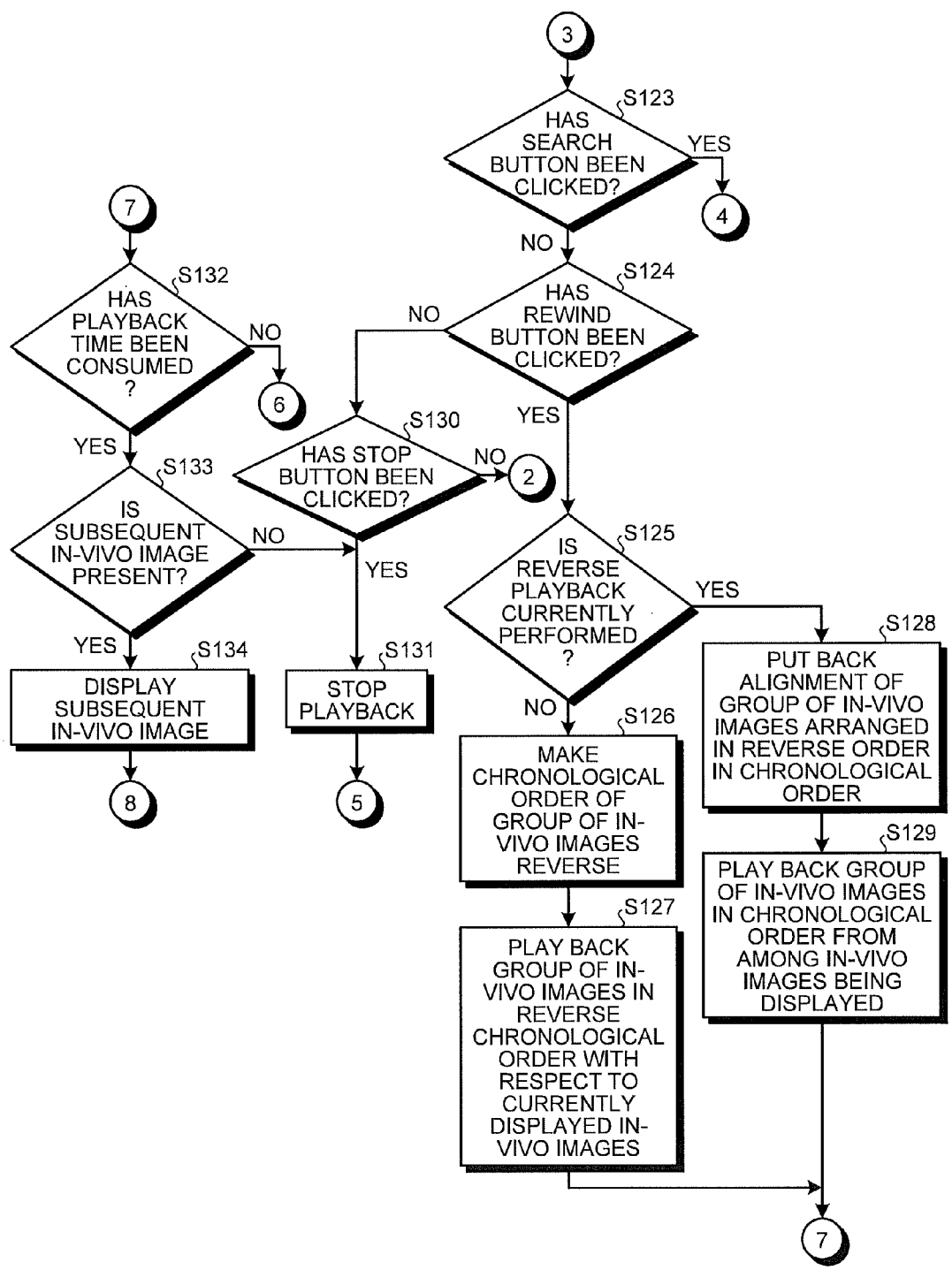
FIG. 9 is a flowchart illustrating another part of the flow of the method of confirming the image interpretation process according to the first embodiment of the present invention.

In contrast, if the result of the determination at Step S121 is that the fast forward button D15d is not clicked (No at Step S121), the control unit 101 move to Step S123 in FIG. 9. At Step S123, the control unit 101 determines whether a user clicks the search button D15a using the pointer P1 (Step S123). If the search button D15a is clicked (Yes at Step S123), the control unit 101 returns to Step S103 in FIG. 7 and subsequently starts the playback of the in-vivo images from the top.

If the result of the determination at Step S123 is that the search button D15a is not clicked (No at Step S123), the control unit 101 then determines whether a user clicks the rewind button D15f using the pointer P1 (Step S124). If the result of the determination at Step S124 is that the rewind button D15f is clicked (Yes at Step S124), the control unit 101 subsequently determines whether the in-vivo images are currently being rewound (reverse playback) (Step S125). If the in-vivo images are not in reverse playback (No at Step S125), the control unit 101 makes chronological order of the group of in-vivo images read at Step S101 in FIG. 7 reverse (Step S126). Furthermore, by using the playback function 111a, the control unit 101 plays back the group of in-vivo images in reverse chronological order with respect to the currently displayed in-vivo images (Step S127). Then, the control unit 101 moves to Step S132 in FIG. 9.

In contrast, if the result of the determination at Step S125 is that the reverse playback is currently being performed (Yes at Step S125), the control unit 101 puts back the alignment of the group of in-vivo images, which is aligned in reverse order, in chronological order (Step S128), and then plays back, using the playback function 111a, the group of in-vivo images in chronological order from among the in-vivo images that are being displayed (Step S129). Thereafter, the control unit 101 moves to Step S132 in FIG. 9.

If the result of the determination at Step S124 is that the rewind button D15f is not clicked (No Step S124), the control unit 101 determines whether a user clicks the stop button D15g using the pointer P1 (Step S130). If the stop button D15g is clicked (Yes at Step S130), the control unit 101 allows the playback function 111a to stop the playback that is currently being performed (Step S131) and then moves to Step S144 in FIG. 10. In contrast, if the stop button D15g is not clicked (No at Step S130), the control unit 101 moves to Step S135 in FIG. 10.

At Step S132 in FIG. 9, which is performed after Step S116, S118, S120, S122, S127, or S129, the control unit 101 determines whether the playback time that is currently set with respect to the in-vivo images being displayed has been consumed (Step S132). If the playback time has not been consumed, i.e., the playback time still remains (No at Step S132), the control unit 101 returns to Step S107 in FIG. 7. In contrast, if the playback time has been consumed (Yes at Step S132), the control unit 101 determines whether there is a subsequent in-vivo image in chronological order to be displayed (Step S133). If the result of the determination at Step S133 is that a subsequent in-vivo image to be displayed is present (Yes Step S133), the control unit 101 allows the playback function 111a to display the subsequent in-vivo image (Step S134) and then moves to Step S104 in FIG. 7. In contrast, if the result of the determination at Step S133 is that the subsequent in-vivo image is not present, i.e., all of the in-vivo images have been displayed (No at Step S133), the control unit 101 moves to Step S131; stops playing the group of in-vivo images (Step S131); and then moves to Step S144 in FIG. 10.

If the result of the determination at Step S102 is that the playback button D15e is not clicked (No at Step S102) or if the result of the determination at Step S130 is that the stop button D15g is not clicked, the control unit 101 determines whether a user clicks the average-color bar button D22 using the pointer P1 (Step S135). If the result of the determination at Step S135 is that the average-color bar button D22 is clicked (Yes at Step S135), the control unit 101 calls the average-color display function 112a in the support function group 112 and allows the average-color display function 112a to create the average-color bar D16 with respect to the group of in-vivo images (Step S136). Furthermore, the control unit 101 embeds the created average-color bar D16 in a predetermined area of the image interpretation screen D1 (Step S137), and then updates the display unit 105 using the image interpretation screen D1 in which the average-color bar D16 has been embedded (Step S138). Then, the control unit 101 moves to Step S144 in FIG. 10.

In contrast, if the result of the determination at Step S135 is that the average-color bar button D22 is not clicked (No at Step S135), the control unit 101 determines whether a user clicks the overview button D23 using the pointer P1 (Step S139). If the overview button D23 is clicked (Yes at Step S139), the control unit 101 creates an overview screen that displays all or part of thumbnail images of the group of in-vivo images in chronological order (Step S140) and displays them on the display unit 105 (Step S141). Then, the control unit 101 determines whether a user inputs, using the operating unit 104, an instruction to return to the image interpretation screen D1 (Step S142). If an instruction to return to the image interpretation screen D1 is input (Yes at Step S142), the control unit 101 displays the image interpretation screen D1 (Step S143) and then moves to Step S144. The overview screen is displayed until the screen returns to the image interpretation screen D1 (No at Step S142).

Figure 10:
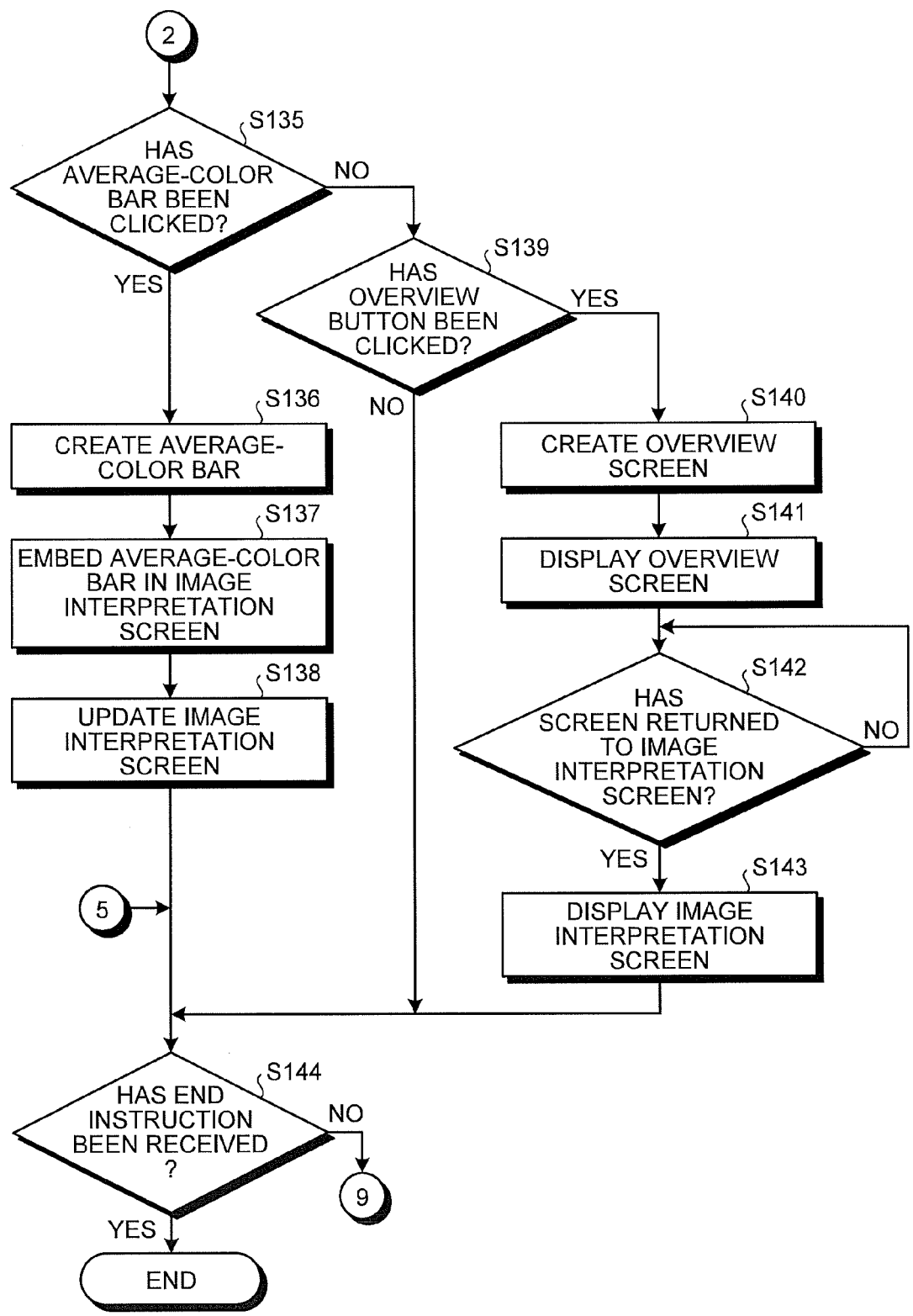
FIG. 10 is a flowchart illustrating another part of the flow of the method of confirming the image interpretation process according to the first embodiment of the present invention.

At Step S144 in FIG. 10, the control unit 101 determines whether a user inputs, using the operating unit 104, an instruction to end the image interpretation program 110 (Step S144). If the instruction is input (Yes at Step S144), the control unit 101 ends the image interpretation program 110 and then ends the image interpretation support operation. In contrast, an instruction to end the image interpretation program 110 is not input (No at Step S144), the control unit 101 returns to Step S102 and similarly performs the process at Step S102 and the subsequent processes.

As described above, because the information processing unit 100 has a function of recording an image interpretation process performed by an image interpreter and a function of visually representing the image interpretation, a user can easily check the image interpretation process that is previously performed by the user himself/herself or another image interpreter. Accordingly, it is possible to ensure a reduction in time or effort that is used when a user again performs image interpretation and to ensure the accuracy of the image interpretation result. For example, in a case in which image interpretation is performed by another image interpreter or by an external image interpreter, it is preferable to check all of the operation contents of image interpretation and to check whether the image interpretation is correctly performed. However, in the first embodiment of the present invention, because the operation contents of the image interpretation, i.e., the operation contents of the information processing unit 100 are visually represented using the image interpretation process bar D17, it is possible to appropriately meet such requirements. Furthermore, even if an unskilled image interpretation user, such as a beginner, attempts to learn a technique of a skilled user, it is hard for the unskilled user to know a procedure or a point of view that is used when the skilled user performs the image interpretation. However, in the first embodiment of the present invention, the image interpretation process bar D17 is displayed as one way of knowing a procedure or a point of view that is used when the skilled user performs the image interpretation. Accordingly, an unskilled image interpretation user can easily learn an image interpretation technique.

Modification 1-1

Figure 11:
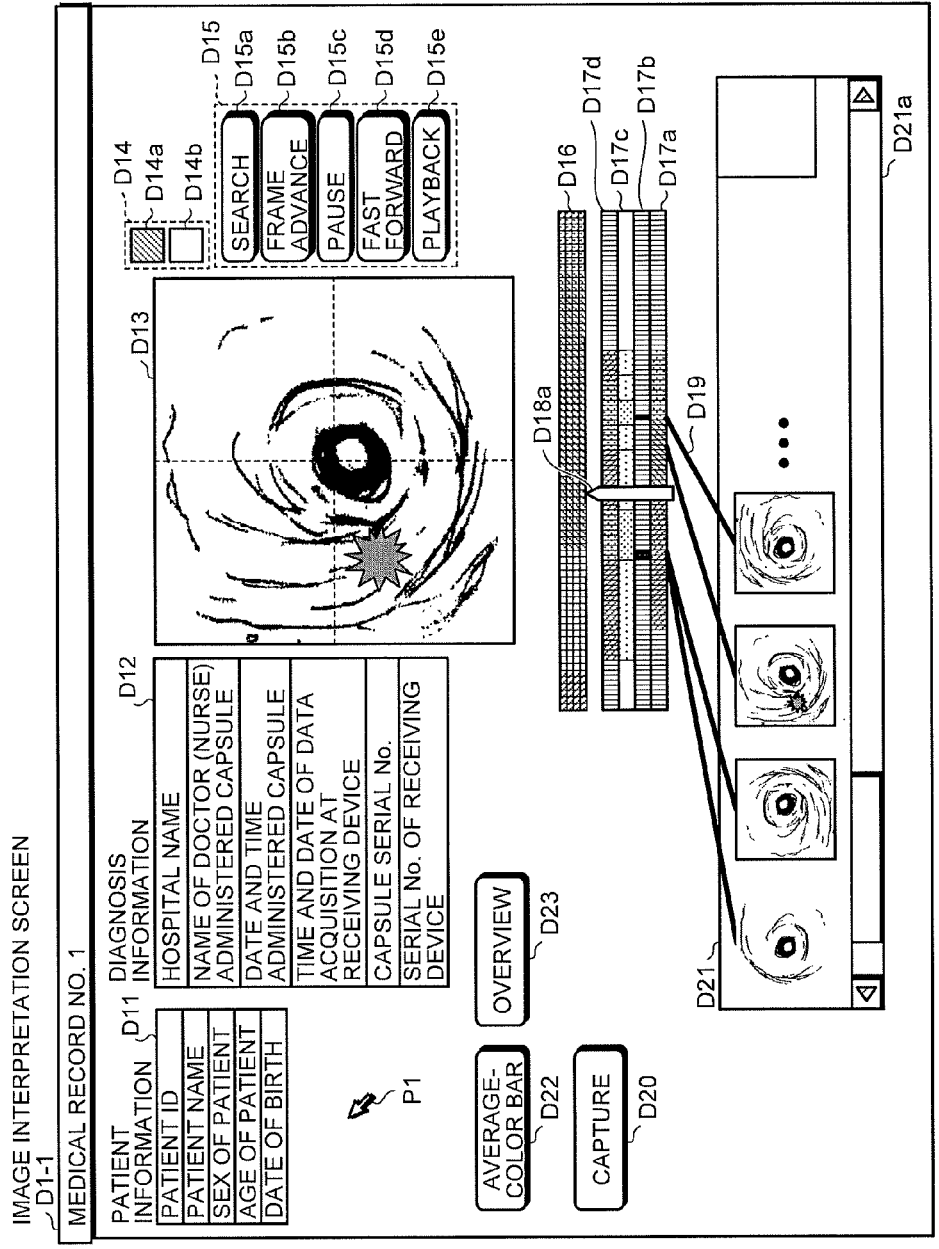
FIG. 11 is a schematic diagram illustrating an example of an image interpretation screen of an image display apparatus according to modification 1-1 of the first embodiment of the present invention.

In the first embodiment described above, a single image interpretation process bar D17 is embedded in a single image interpretation screen D1; however, the present invention is not limited thereto. For example, as an example of an image interpretation screen D1-1 according to modification 1-1 of the first embodiment of the present invention illustrated in FIG. 11, image interpretation process bars D17a to D17d of different kinds of image interpretation operation data can be vertically aligned.

Specifically, in the modification 1-1 of the first embodiment of the present invention, an image interpretation operation recording unit constituted of the operation monitoring unit 114, the display time measuring unit 115, and the memory unit 102 records a plurality of pieces of image interpretation operation data each having a different content with respect to the same image interpretation; the image interpretation process bar creating unit 116 creates, using one or the plurality of pieces of image interpretation operation data each having a different content, the image interpretation process bars D17a to D17d for each pieces of image interpretation operation data each having a different content; and the image interpretation operation image display unit constituted of the control unit 101 and the display unit 105 displays the image interpretation process bars D17a to D17d for each image interpretation operation data having a different content.

Accordingly, a user can simultaneously and visually recognize multiple pieces of image interpretation operation. Furthermore, the image interpretation process bars D17a to D17d vertically arranged are preferably associated with the time axes. Specifically, the image interpretation operation image display unit constituted of the control unit 101 and the display unit 105 preferably displays the image interpretation process bars D17a to D17d for each piece of image interpretation operation data having a different content while ordering is associated with each of the image interpretation process bars D17a to D17d for each image interpretation operation. At this time, the image interpretation process bar creating unit 116 in the control unit 101 can create, using a different color or pattern for each image interpretation, the image interpretation process bars D17a to D17d for each image interpretation. In such a case, it is possible to display a single slider D18a that can move along the average-color bar D16 on the image interpretation process bars D17a to D17d.

Modification 1-2

Figure 12:
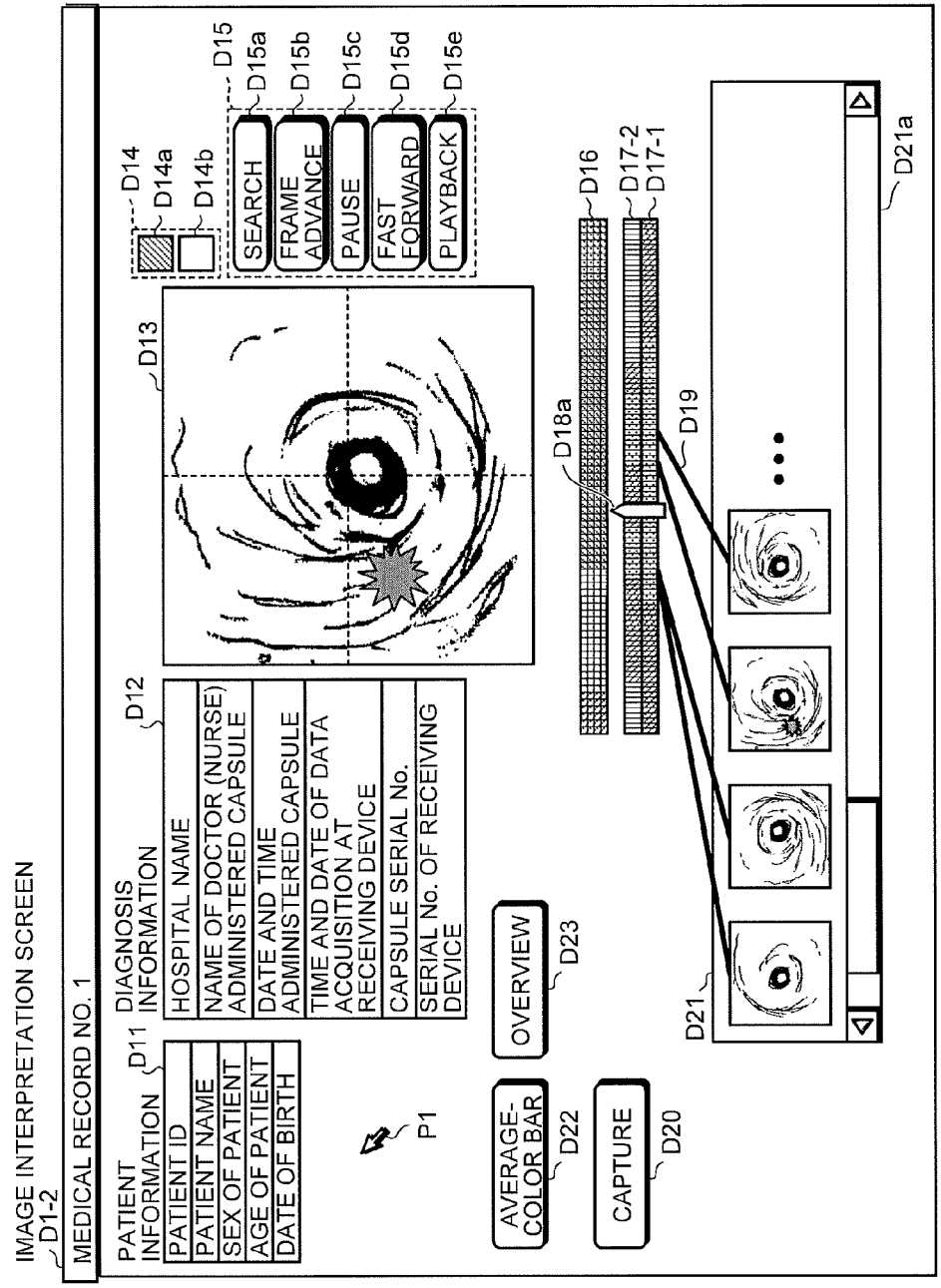
FIG. 12 is a schematic diagram illustrating an example of an image interpretation screen of an image display apparatus according to modification 1-2 of the first embodiment of the present invention.

Furthermore, if a plurality of image interpretation process bars D17 is embedded in a single image interpretation screen, instead of using the image interpretation process bars D17a to D17d for the different image interpretation operation data, as an example of an image interpretation screen D1-2 according to modification 1-2 of the first embodiment of the present invention illustrated in FIG. 12, the embedded image interpretation process bar D17 can be, for example, image interpretation process bars D17-1 and D17-2 that are created in accordance with the image interpretation operation data obtained when different image interpretation performed on the same in-vivo image group.

Specifically, in the modification 1-2 of the first embodiment of the present invention, an image interpretation operation recording unit constituted of the operation monitoring unit 114, the display time measuring unit 115, and the memory unit 102 records image interpretation operation data for each different image interpretation operation; an image interpretation operation image creating unit constituted of the image interpretation process bar creating unit 116 in the control unit 101 creates, using one piece or a plurality of pieces of image interpretation operation data for each image interpretation operation, the image interpretation process bars D17-1 and D17-2 that are images for each image interpretation operation; and an image interpretation operation image display unit constituted of the control unit 101 and the display unit 105 displays the image interpretation process bars D17-1 and D17-2 for each image interpretation operation.

With this configuration described above, in the modification 1-2 of the first embodiment of the present invention, a user can simultaneously and visually recognizes a plurality of previous image interpretation processes. The image interpretation process bars D17-1 to D17-2 vertically arranged are preferably associated with time axes. Furthermore, with the image interpretation process bars that are vertically arranged and displayed, it is preferable that the latest image interpretation process bar is preferably arranged on the uppermost or the lowermost line from among the bars, and the rest of image interpretation process bars are preferably arranged in chronological order of the image interpretation operation below or above the latest image interpretation process bar. In other words, the image interpretation process bars D17-1 and D17-2 are preferably displayed for each image interpretation operation while the image interpretation operation data display unit constituted of the control unit 101 and the display unit 105 associates the ordering with the image interpretation process bars D17-1 and D17-2 for each image interpretation operation. At this time, the image interpretation process bar creating unit 116 in the control unit 101 can create, using a different color or pattern for each image interpretation operation, the image interpretation process bars D17-1 D17-2 for each image interpretation operation.

Modification 1-3

In the first embodiment or the modifications thereof, the image interpretation process bar D17 is created using image interpretation operation data for each single image interpretation; however, the present invention is not limited thereto. For example, the image interpretation process bar can be created in accordance with the average of image interpretation operation data that is obtained from a plurality of pieces of image interpretation performed on the same in-vivo image. In the following, such a case will be described, as modification 1-3 of the first embodiment of the present invention, in detail with reference to the drawings. However, a detailed description of components having the same configurations and operations as those described in the first embodiment will be omitted by quoting or referring thereto.

Figure 13:
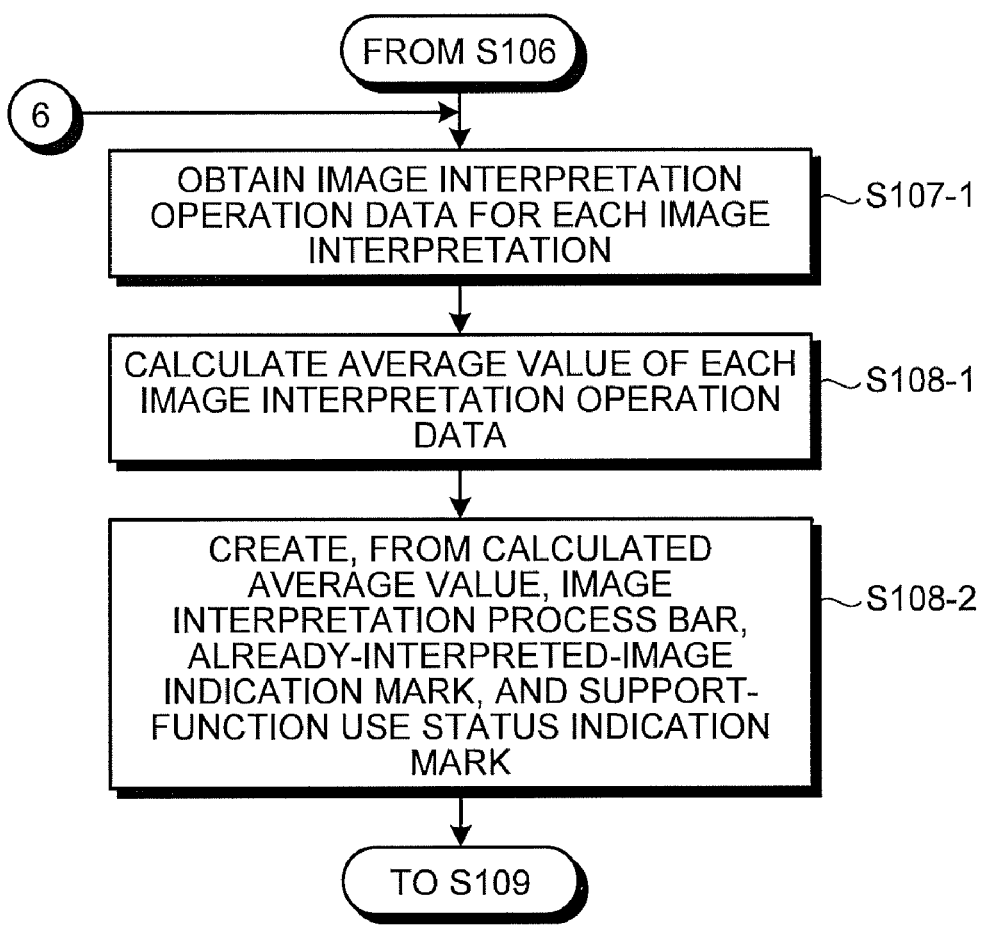
FIG. 13 is a part of the flowchart illustrating the flow of a method of confirming an image interpretation process using an image display apparatus according to modification 1-3 of the first embodiment of the present invention.

FIG. 13 is a part of the flowchart illustrating the flow of a method of confirming an image interpretation process using an image display apparatus according to the modification 1-3 of the first embodiment of the present invention. Because other operations are the same as those described in the above-described first embodiment with reference to FIGS. 7 to 10, a description thereof in detail will be omitted here. As illustrated in FIG. 13, in the modification 1-3 of the first embodiment of the present invention, Steps S107 and S108 of the method of confirming the image interpretation process illustrated in FIGS. 7 to 10 are replaced by Steps S107-1, S108-1, and S108-2.

At Step S107-1, the control unit 101 obtains image interpretation operation data that is stored, for each image interpretation, in the memory unit 102. Then, the control unit 101 calculates the average value of the image interpretation operation data that is obtained for each image interpretation (Step S108-1) and subsequently creates, in accordance with the calculated average value of the image interpretation operation data, the image interpretation process bar D17, the already-interpreted-image indication mark D14a, and the support-function use status indication mark D14b (Step S108-2). Thereafter, the control unit 101 moves to Step S109 that is described in the first embodiment and performs the subsequent processes in a similar manner as in the first embodiment.

As described above, in the modification 1-3 of the first embodiment of the present invention, the image interpretation process bar creating unit 116 in the control unit 101 also functions as an average value calculating unit that calculates the average value of the value of a plurality of pieces of image interpretation operation data recorded for each different image interpretation in the image interpretation operation recording unit constituted of the operation monitoring unit 114, the display time measuring unit 115, and the memory unit 102. Furthermore, the image interpretation process bar creating unit 116 in the control unit 101 creates the image interpretation process bar D17 using the average value calculated by the average value calculating unit. With this operation, in the modification 1-3 of the first embodiment, a user can recognize, at a glance, a reliable image interpretation process using the average of the image interpretation performed multiple times. Accordingly, it is possible to further reduce the time or effort that is used when a user again performs image interpretation and to more appropriately educate an unskilled image interpretation user.

If the image interpretation operation data indicates the display time or the playback speed of each in-vivo image, the average value mentioned here can be, for example, an average value of a plurality of pieces of display time or an average value of playback speeds of the same or the associated in-vivo image. If the image interpretation operation data indicates display history information, the average value can be the probability of displaying the same or associated in-vivo image with respect to the number of times the image interpretation is performed.

Furthermore, for the image interpretation operation data that is used to calculate the average value, in addition to the image interpretation operation data obtained at the time of previous image interpretation, it is also possible to include image interpretation operation data obtained at the time of currently processed image interpretation. Furthermore, it is also possible to configure the image interpretation operation data that is used to calculate the average value such that, for example, a user can select that data in accordance with a parameter, such as an image interpretation ID that is automatically assigned to each image interpretation operation at the commencement of the image interpretation or an image interpreter ID that is assigned to an image interpreter in advance. Because the other configurations and operations are the same as those in the embodiment or the modifications thereof described above, a description thereof in detail will be omitted here.

Modification 1-4

For example, the image interpretation operation data can be recorded in the memory unit 102 for each image interpreter, each subject, or each subject's case. In such a case, it is possible to set priority for each image interpreter, each subject, or each subject's case. In the first embodiment described above, when creating the image interpretation process bar D17 to be embedded in the image interpretation screen D1, by setting priority to image interpretation operation data, it is possible to automatically use high-priority image interpretation operation data. Furthermore, in the modification 1-2 described above, the image interpretation process bars D17-1 to D17-2 can be vertically arranged in priority order. Furthermore, in the modification 1-3 described above, when calculating the average value of image interpretation operation data, it is possible to weight the image interpretation operation data in accordance with the priority.

The priority of each image interpretation operation data can be set because the control unit 101 functions as a priority adding unit that adds priority for each image interpretation operation data. At this time, priority can be freely set by a user; can be set to each image interpreter, each subject, or each subject's case; or can be automatically or manually given using the priority that is given, in advance, to the content of the image interpretation operation data, such as a playback speed or an image interpretation support function. For example, with the image interpretation support function, priority can be set in the order of an express view function, the average-color display function 112a, the overview function 112b, the automatic speed regulation function, and a normal display function. It is possible to automatically give priority to the image interpretation operation data in accordance with which one of them is used.

Second Embodiment

Figure 14:
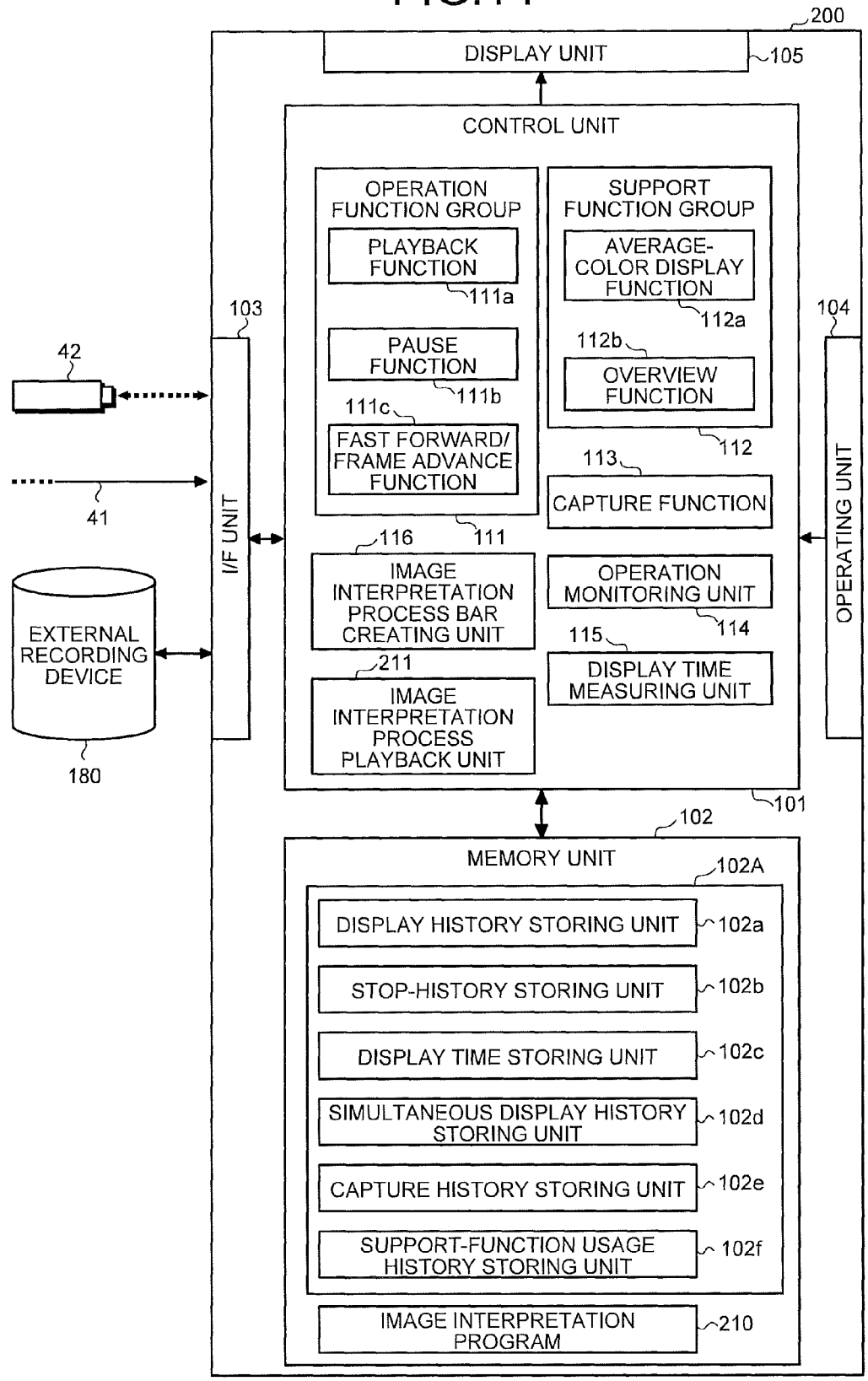
FIG. 14 is a block diagram illustrating, in outline, the configuration of an information processing unit corresponding to an image display apparatus according to a second embodiment of the present invention.

The configuration and the operation of an image display apparatus according to a second embodiment of the present invention will be described in detail with reference to the drawings. In the second embodiment of the present invention, the capsule endoscope system 1 that is the same as that described in the first embodiment described above will be described as an example. However, in the second embodiment, the information processing unit 100 according to the first embodiment is replaced by an information processing unit 200 illustrated in FIG. 14. Furthermore, in the following description, components that are identical to those in the first embodiment or the modifications thereof described above are assigned the same reference numerals, and a detailed description thereof is omitted. FIG. 14 is a block diagram illustrating, in outline, the configuration of the information processing unit 200 according the second embodiment of the present invention. The information processing unit 200 corresponds to an image display apparatus according to the second embodiment of the present invention.

As illustrated in FIG. 14, with the information processing unit 200 according to the second embodiment of the present invention, an image interpretation program 210 is executed in the control unit 101 as an image interpretation support program. In the image interpretation program 210, the configuration that implements an image interpretation process playback unit 211 is added to the configuration of the image interpretation program 110 according to the first embodiment described above. By using image interpretation operation data obtained when the previous image interpretation performed on a group of in-vivo images read from the memory unit 102 by the control unit 101, the image interpretation process playback unit 211 implements the function of reproducing, in accordance with playback of in-vivo images, various operations performed at the time of image interpretation.

Figure 15:
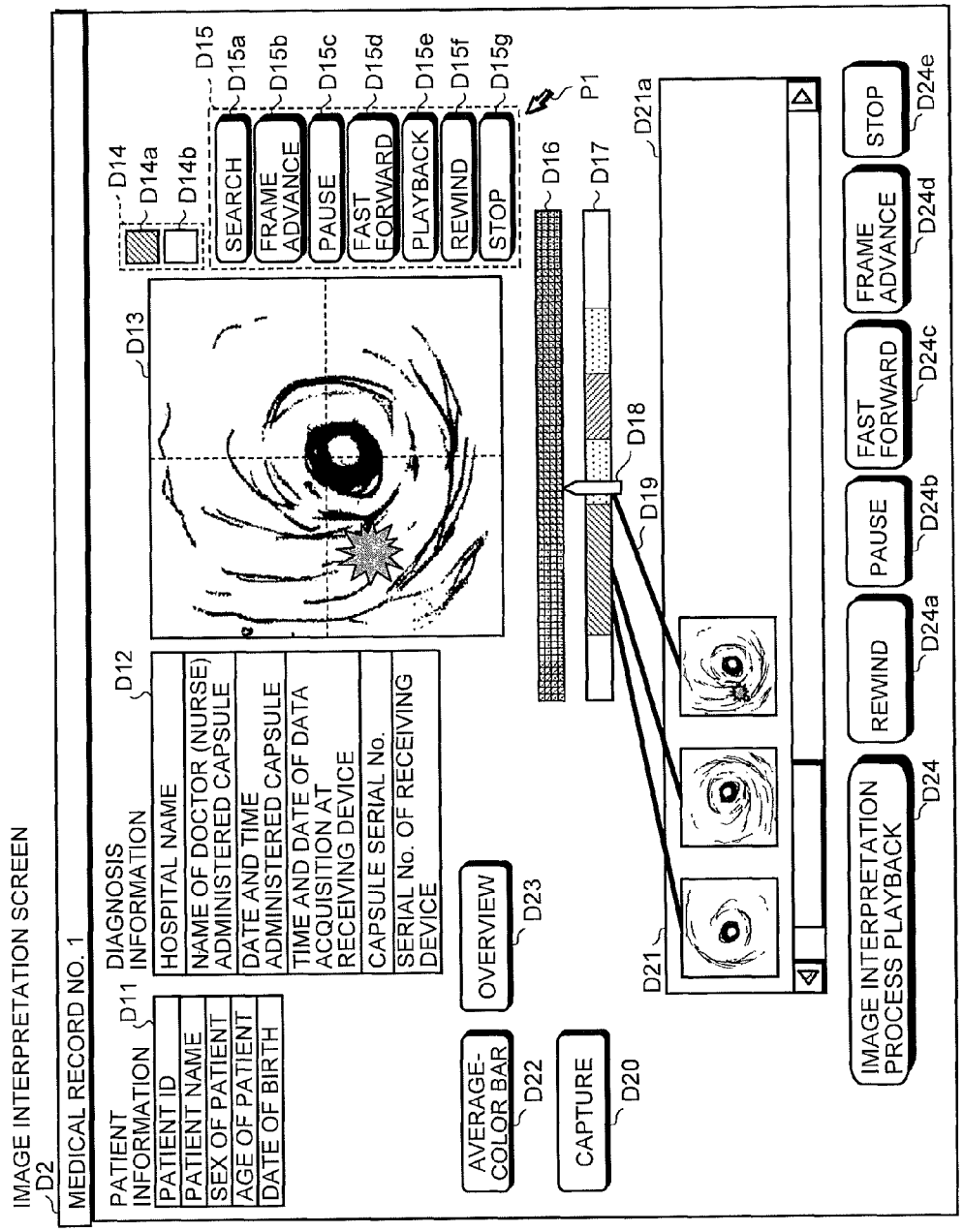
FIG. 15 is a schematic diagram illustrating an example of an image interpretation screen according to the second embodiment of the present invention.

FIG. 15 is a schematic diagram illustrating an example of an image interpretation screen D2 according to the second embodiment of the present invention. As illustrated in FIG. 15, in addition to the various functions embedded in the image interpretation screen D1 illustrated in FIG. 5, an image interpretation process playback button D24 that reproduces the previous image interpretation process is embedded in the image interpretation screen D2. If a user operates the pointer P1 using the operating unit 104 and clicks an image interpretation process playback button D24, a series of in-vivo images is played in the main display area D13 in accordance with the playback operation performed at the time of previous image interpretation, such as forward playback, reverse playback, pause, fast forward, and frame advance. At this time, an instruction operation of a function according to the operation of a button, such as the capture button D20, the average-color bar button D22, or the overview button D23, is also reproduced.

Furthermore, as an operation button for playback of the image interpretation process, a rewind button D24a, a pause button D24b, a fast forward button D24c, a frame advance button D24d, and a stop button D24e are embedded in the image interpretation screen D2. If a user clicks the rewind button D24a using the pointer P1, an image interpretation process that is currently being reproduced on the image interpretation screen D2 is rewound, i.e., is played back in reverse. Similarly, if a user clicks, using the pointer P1, the pause button D24b, the fast forward button D24c, the frame advance button D24d, or the stop button D24e, the image interpretation process that is currently being reproduced on the image interpretation screen D2 is paused, fast forwarded, frame advanced, or stopped.

As described above, according to the second embodiment of the present invention, the previous operation of the image interpretation and the image interpretation process are realistically reproduced on the image interpretation screen D2. Accordingly, a user can check easily and with reality the image interpretation process performed by another image interpreter using the reproduced image interpretation process. Because the previous image interpretation is realistically reproduced, it is possible to appropriately evaluate that image interpretation or that image interpreter. Furthermore, because the image interpretation process is realistically reproduced, it is useful for a user as an educational material for learning image interpretation.

Because the other configurations and operations are the same as those in the embodiment or the modifications thereof described above, a description thereof in detail will be omitted here.

Modification 2-1

In the second embodiment described above, the image interpretation process playback unit 211 reproduces, on the image interpretation screen D2, image interpretation operation data that is read from the memory unit 102 without processing anything. Therefore, if image interpretation operation data of image interpretation performed for multiple times on a single in-vivo image group is accumulated in the memory unit 102 because image interpretation is performed for multiple times on a single in-vivo image group, a user is required to select which image interpretation process is reproduced; however, the present invention is not limited thereto. For example, in a similar manner as in the modification 1-3 of the first embodiment described above, it is also possible to configure the information processing unit 200 such that the average value of image interpretation operation data of image interpretation performed for multiple times is calculated and is reproduced on the image interpretation screen D2.

A method of calculating the average value using the image interpretation operation data of image interpretation performed for multiple times is the same as that in the modification 1-3 of the first embodiment described above. A method of reproducing the image interpretation process on the image interpretation screen D2 using the calculated average value is the same as that in the second embodiment described above. Accordingly, a description thereof in detail will be omitted here.

Modification 2-2

In a similar manner as in modification 1-4 of the first embodiment described above, if priority is set for each image interpreter, each subject, or each subject's case, it is also possible to configure the information processing unit 200 such that an image interpretation process to be reproduced is automatically selected in accordance with that priority.

Third Embodiment

In the following, the configuration and the operation of a capsule endoscope system and an image interpretation support system that include an image display apparatus according to a third embodiment of the present invention will be described in detail with reference to the drawings. In the third embodiment, the capsule endoscope system 1 that is the same as that in the first embodiment described above will be described as an example. However, in the third embodiment of the present invention, the information processing unit 100 according to the first embodiment is replaced by a request-source information processing unit 310, which will be described later. The request-source information processing unit 310 corresponds to an image display apparatus according to the third embodiment. Furthermore, in the following description, components that are identical to those in the first embodiment, the second embodiment, or the modifications thereof described above are assigned the same reference numerals, and a detailed description thereof is omitted.

In general, with a capsule endoscope system, a large number of in-vivo images, corresponding to about as many as 60,000 images, i.e., about eight hours when converted to playback time, of a subject are captured in a single observation. Accordingly, with the image interpretation operation that is performed on a group of in-vivo images and that is obtained in a single observation, an enormous number of in-vivo images need to be subjected to image interpretation. Accordingly, by allowing different image interpreters to perform image interpretation for each portion of a group of in-vivo images on the time axis or on the path inside the subject, it is possible to reduce the burden imposed on one image interpreter at the time of image interpretation. For example, by outsourcing a part of the image interpretation performed on a group of in-vivo images to an outside doctor or health professional and by allowing the rest of image interpretation to be performed by an in-house image interpreter, it is possible to reduce the burden imposed on the in-house image interpreter at the time of image interpretation.

However, with the conventional capsule endoscope system, part of a group of in-vivo images cannot be cut out while maintaining the ordering thereof in chronological order. Accordingly, if data of the group of in-vivo images is transmitted to another image interpreter by mail, a large-capacity storage medium, such as a DVD-RAM, is required. Furthermore, for example, if an image interpretation request is sent via a network, an enormous amount of network traffic occurs. Accordingly, there is a possibility of temporary occurrence of a jam in the network.

Even if a part of the group of in-vivo images is cut out while maintaining the ordering thereof in chronological order, it is not possible to embed, in image interpretation operation data of the original group of in-vivo images obtained at the time of image interpretation, image interpretation operation data of the cut out portion obtained at the time of image interpretation while maintaining the ordering thereof in chronological order.

In the third embodiment of the present invention, it is possible to make an image interpretation request by cutting out a part of an in-vivo image in a group of in-vivo images while maintaining the ordering thereof in chronological order. Furthermore, for example, it is possible to embed, in image interpretation operation data of the original group of in-vivo images obtained at the time of image interpretation, image interpretation operation data of a part of the in-vivo image that is obtained at the time of image interpretation and is requested outside for image interpretation while maintaining the ordering thereof in chronological order.

Figure 16:
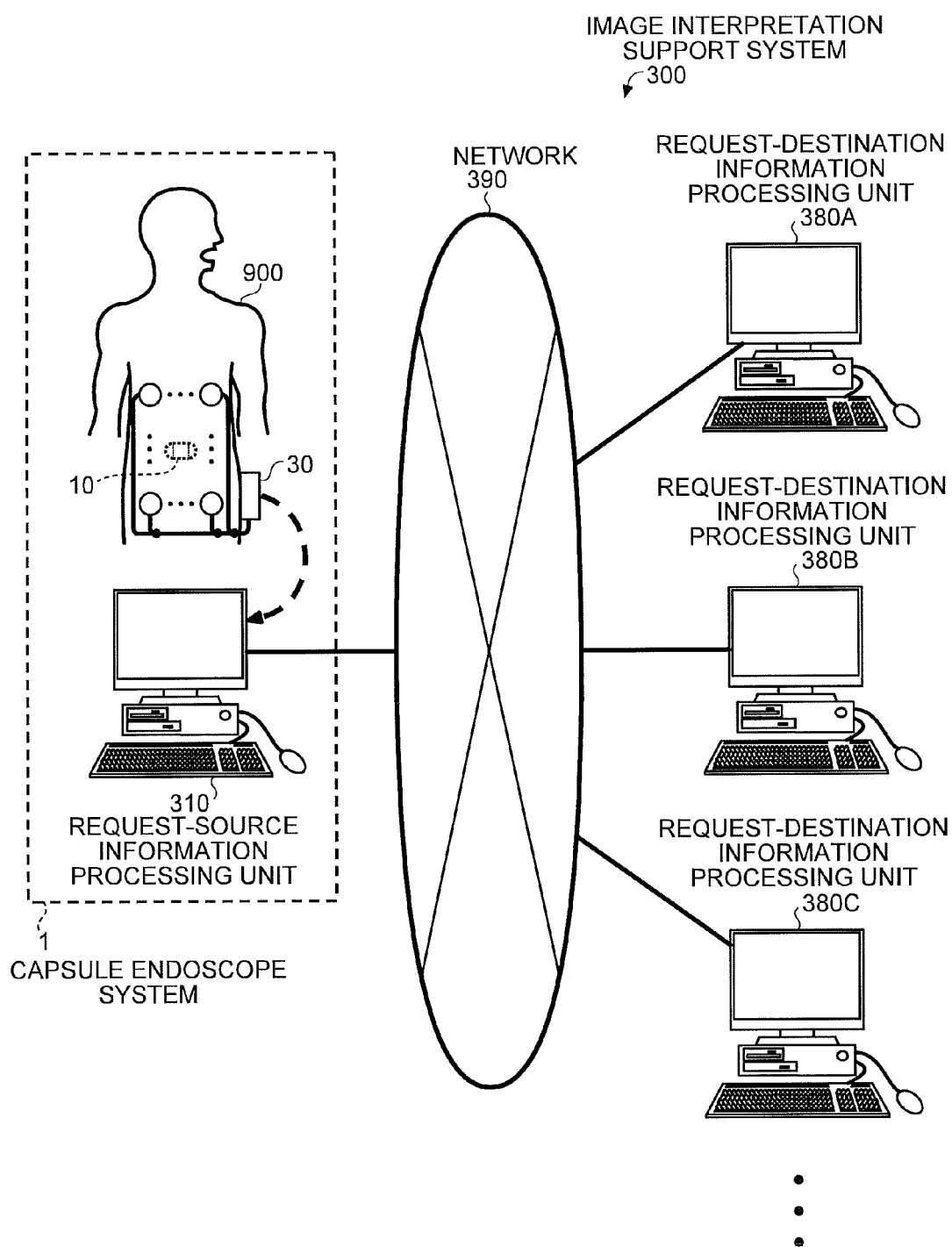
FIG. 16 is a schematic diagram illustrating, in outline, the configuration of an image interpretation support system according to a third embodiment of the present invention.

FIG. 16 is a schematic diagram illustrating, in outline, the configuration of an image interpretation support system 300 according to the third embodiment of the present invention. As illustrated in FIG. 16, in the image interpretation support system 300, the capsule endoscope system 1 is connected to request-destination information processing units 380A to 380C . . . via a network 390, which are capable of communicating each other. In the following description, a reference numeral 380 denotes a given request-destination information processing unit.

It is possible to use various networks for the network 390, such as the Internet, a local area network (LAN), a wide area network (WAN), or a dedicated line using a Japanese Bankers Association standard communication protocol. Furthermore, it is possible to use an information processing unit, such as a personal computer or a workstation, for a request-destination information processing unit 380.

Figure 17:
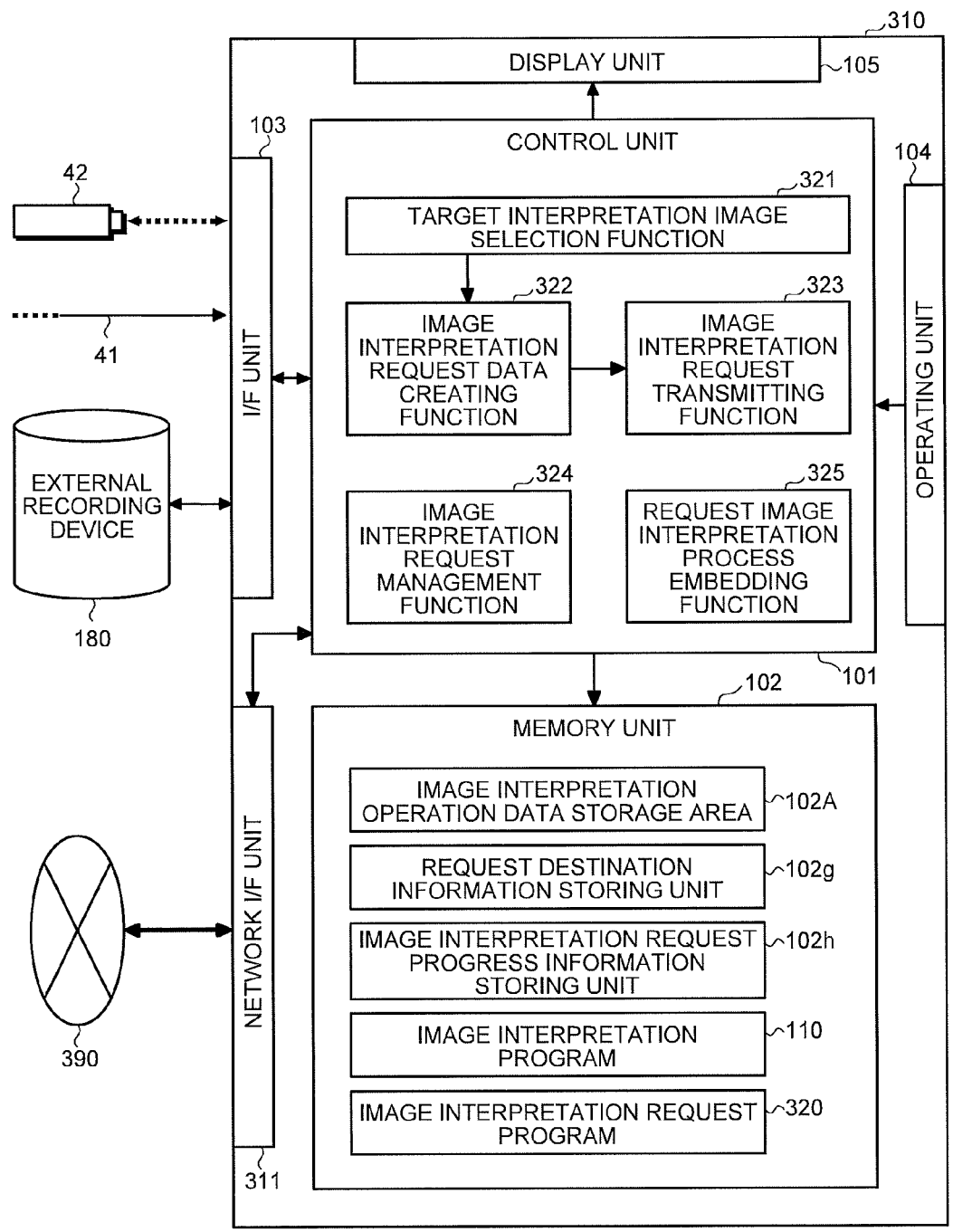
FIG. 17 is a schematic diagram illustrating, in outline, the configuration of a request-source information processing unit corresponding to an image display apparatus according to the third embodiment of the present invention.

FIG. 17 is a schematic diagram illustrating, in outline, the configuration of the request-source information processing unit 310 according to the third embodiment. As illustrated in FIG. 17, the request-source information processing unit 310 has a configuration in which a network I/F unit 311 is added to the information processing unit 100 according to the embodiments or the modifications thereof described above. In other words, in the third embodiment of the present invention, a network communication function is added to the information processing unit 100. The network I/F unit 311 can be a commonly used communication unit, such as Network Internet Card (NIC).

Furthermore, as illustrated in FIG. 17, in addition to the image interpretation program 110, an image interpretation request program 320 is executed in the control unit 101 in the request-source information processing unit 310. In addition to the image interpretation operation data storage area 102A, the memory unit 102 in the request-source information processing unit 310 includes a request destination information storing unit 102g that stores therein information on an image interpreter registered as a request destination, such as a name or a title, an address or whereabouts, and a contact address, such as an email address or a facsimile number and includes an image interpretation request progress information storing unit 102h that stores therein progress information on image interpretation that is performed on in-vivo images and that is requested outside. The progress information on the image interpretation preferably contains, for example, information whether an image interpretation request has been made or not; a request destination; a request day of image interpretation; a request method, such as mail or communication; a reply due date of an image interpretation result; and a reply date of an image interpretation result.

The image interpretation request program 320 is stored in, for example, the memory unit 102 and the control unit 101 appropriately reads and executes the image interpretation request program 320, thus implementing its function. The following functions are implemented in the control unit 101 that executes the image interpretation request program 320: a target interpretation image selection function 321 that implements a function of selecting, from among a series of in-vivo images, a target in-vivo image for an image interpretation request; an image interpretation request data creating function 322 that creates image interpretation request data of the selected in-vivo image; an image interpretation request transmitting function 323 that transmits the created image interpretation request data to a request-destination information processing unit 380 via the network I/F unit 311; an image interpretation request management function 324 that manages whether an image interpretation request has been made for each in-vivo image; and a request image interpretation process embedding function 325 that embeds, in image interpretation operation data of the original series of in-vivo images, replied image interpretation operation data of an in-vivo image that has been requested for an image interpretation while maintaining the ordering thereof in chronological order. Furthermore, the operation function group 111, the support function group 112, the capture function 113, the operation monitoring unit 114, the display time measuring unit 115, and the image interpretation process bar creating unit 116 illustrated in FIG. 4 are implemented in the control unit 101 that executes the image interpretation program 110; however, they are not illustrated in FIG. 17.

Figure 18:
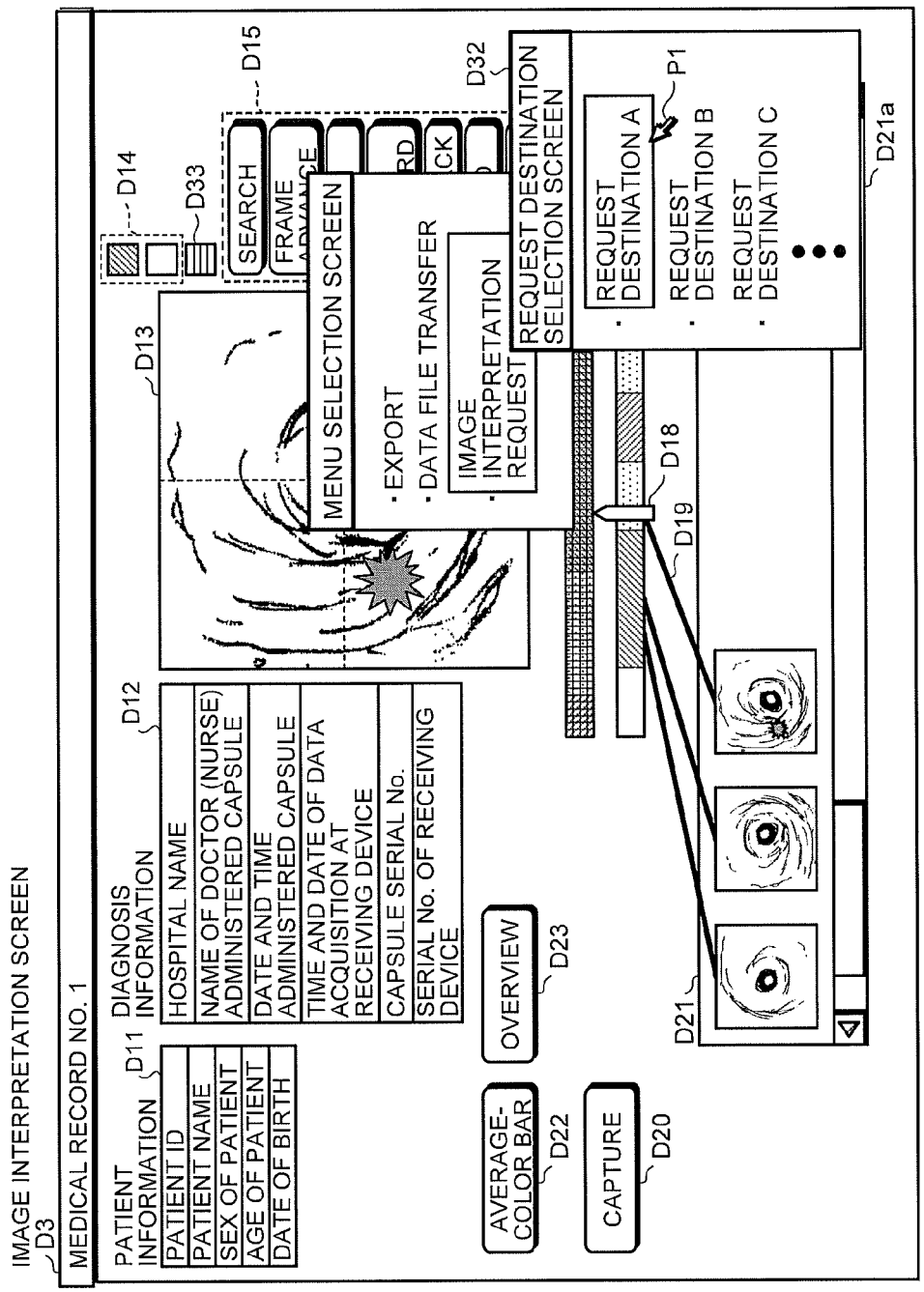
FIG. 18 is a schematic diagram illustrating an example of an image interpretation screen according to the third embodiment of the present invention.

In the following, in the third embodiment of the present invention, the flow of a process for requesting a part of a series of in-vivo images from an outside image interpreter (request destinations A to C . . . ) will be described in detail with reference to the drawings. FIG. 18 is a schematic diagram illustrating an example of an image interpretation screen D3 according to the third embodiment of the present invention.

As illustrated in FIG. 18, in the third embodiment of the present invention, while an in-vivo image to be requested for image interpretation is displayed on the main display area D13, a user moves the pointer P1 using the operating unit 104 onto the main display area D13 and, for example, clicks the right mouse button in this state. By doing so, on the display unit 105, a menu selection screen D31 is displayed, whose upper left corner is a position where the pointer P1 is right clicked. The menu selection screen D31 is a so called context menu. The menu selection screen D31 includes, for example, an export menu for inputting an instruction to output, while maintaining chronological order, data of all of a series of in-vivo images, data of an in-vivo image displayed on the display unit 105, or data of a part of an in-vivo image group including that in-vivo image; a data file transfer menu for inputting an instruction to transfer data of a data file of an in-vivo image that is currently being displayed on the main display area D13; and an image interpretation request menu for inputting an instruction to request image interpretation with respect to an in-vivo image that is currently being displayed on the display unit 105 or with respect to a part of in-vivo image group including that in-vivo image.

If a user moves the pointer P1 onto the image interpretation request menu on the menu selection screen D31, a request destination selection screen D32 is displayed on the display unit 105 at the position close to the image interpretation request menu. The request destination selection screen D32 is a so called context menu. On the request destination selection screen D32, a list of the request destinations registered in the request destination information storing unit 102g in the memory unit 102 is displayed as the request destinations. If a user operates the pointer P1 and selects one of the request destinations on the request destination selection screen D32, the control unit 101 calls the target interpretation image selection function 321; selects the target image; subsequently calls the image interpretation request data creating function 322; creates request data to be transmitted to the request destination; then calls the image interpretation request transmitting function 323; and transmits the created request data to the contact address of the selected request destination, for example, an email address. At this time, request data created by the image interpretation request data creating function 322 contains data of in-vivo image selected by the target interpretation image selection function 321.

If the request data transmitted to the network 390 by the image interpretation request transmitting function 323, the image interpretation request management function 324 that is implemented by the control unit 101 detects it. The image interpretation request management function 324 records, in the image interpretation request progress information storing unit 102h, information indicating that an image interpretation request with respect to a target in-vivo image for an image interpretation request has been made.

Furthermore, in the third embodiment of the present invention, an image interpretation request status indication mark D33 that visually displays information indicating whether an image interpretation request has been previously made for an in-vivo image that is currently being displayed on the main display area D13 or information indicating whether there is a result of the previously requested image interpretation is displayed near the main display area D13 on the image interpretation screen D3. Accordingly, a user can easily and visually recognize the progress of the image interpretation request related to the in-vivo image that is currently being displayed.

Figure 19:
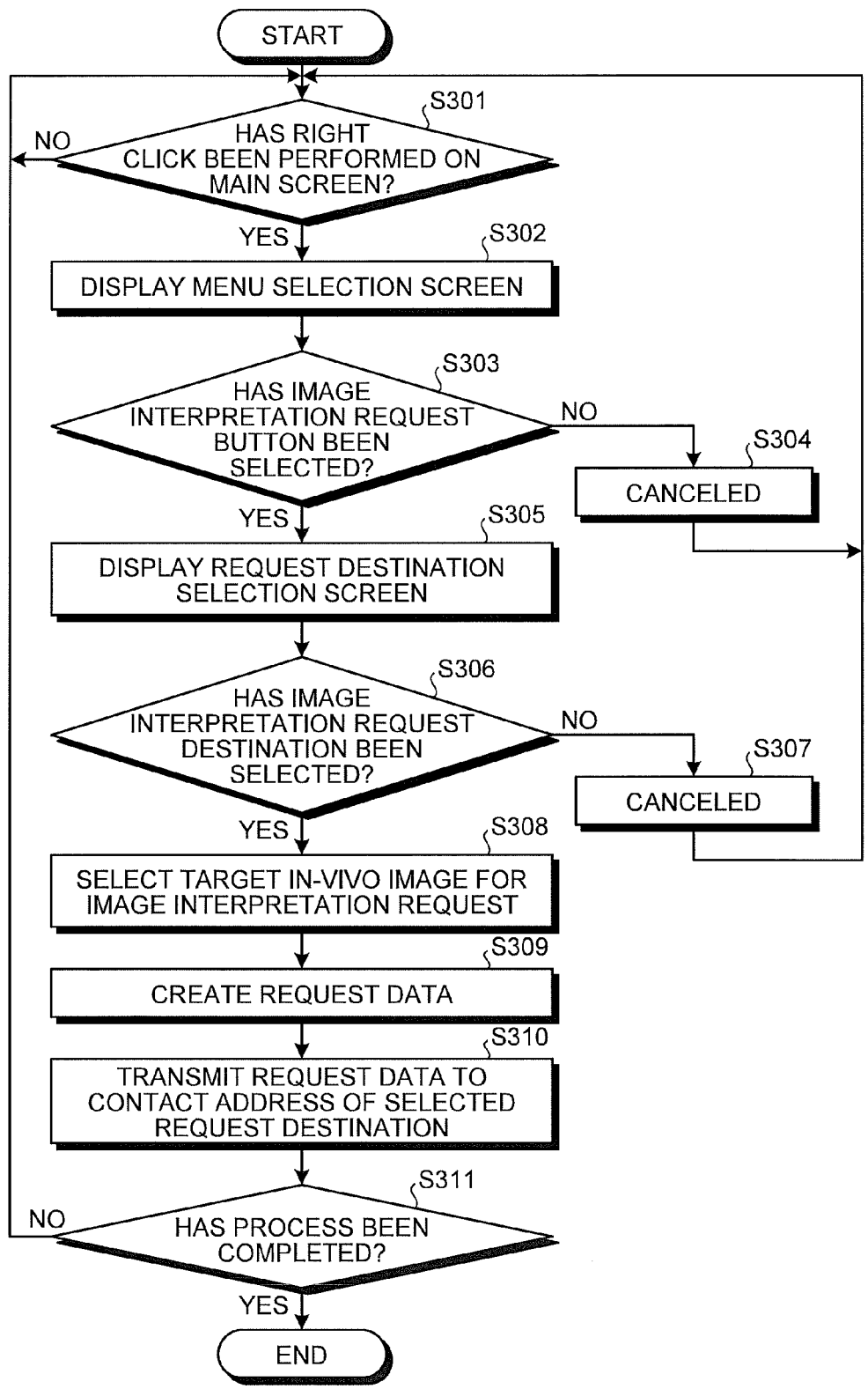
FIG. 19 is a flowchart illustrating the flow of the operation of an image interpretation request according to the third embodiment of the present invention.

In the following, the operation of the image interpretation request according to the third embodiment of the present invention will be described with reference to the drawings. FIG. 19 is a flowchart illustrating the flow of the operation of an image interpretation request according to the third embodiment of the present invention. In the following, a description will be given by focusing on the operation of the control unit 101 that implements the operation for requesting image interpretation by executing the image interpretation request program 320.

As illustrated in FIG. 19, the control unit 101 monitors whether a user operates the pointer P1 using the operating unit 104 and clicks the right mouse button in the main display area D13 (Step S301). If a user does not clicks the right mouse button in the main display area D13 (No at Step S301), the control unit 101 repeats the process of Step S301. In contrast, if a user clicks the right mouse button in the main display area D13 (Yes at Step S301), the control unit 101 displays, on the display unit 105, the menu selection screen D31 whose upper left corner is a position where the pointer P1 is right clicked (Step S302). Subsequently, the control unit 101 determines, using the pointer P1 in a similar manner as the above, whether the image interpretation request button on the menu selection screen D31 is selected (Step S303). If the image interpretation request button is selected (Yes at Step S303), the control unit 101 displays the request destination selection screen D32 near the image interpretation request button (Step S305). If the image interpretation request button is canceled without being selected (No at Step S303), the control unit 101 cancels the display of the menu selection screen D31 (Step S304) and returns to Step S301.

Furthermore, the control unit 101 determines which request destination of image interpretation is selected on the request destination selection screen D32 that is displayed at Step S305 (Step S306). If the request destinations of the image interpretation are canceled without being selected (No at Step S306), the control unit 101 cancels both the display of the request destination selection screen D32 and the menu selection screen D31 (Step S307) and returns to Step S301.

In contrast, if the result of the determination at Step S306 is that any one of the request destinations of the image interpretation is selected (Yes at Step S306), the control unit 101 calls the target interpretation image selection function 321 and selects a target in-vivo image for image interpretation request (Step S308). Subsequently, the control unit 101 calls the image interpretation request data creating function 322 and creates, using image data of the selected in-vivo image, request data to be transmitted to the request destination (Step S309). Furthermore, the control unit 101 calls the image interpretation request transmitting function 323 and transmits the created request data to the contact address of the request destination selected at Step S306, specifically, an email address (Step S310). Then, the control unit 101 determines whether an instruction to end the operation of the image interpretation request is input (Step S311). If it is not input (No at Step S311), the control unit 101 returns to Step S301 and performs the subsequent processes in a similar manner as described above. In contrast, if the result of the determination at Step S311 is that an instruction to end the operation of image interpretation request is input (Yes at Step S311), the control unit 101 ends the operation of the image interpretation request.

As described above, with the request-source information processing unit 310 according to the third embodiment of the present invention, the target interpretation image selection function 321 in the control unit 101 functions as an image cutting-out unit that cuts out a part of a group of in-vivo images while maintaining ordering. Both the image interpretation request data creating function 322 and the image interpretation request transmitting function 323 functions as an image interpretation request transmitting unit that transmits, to the request-destination information processing unit 380 via the network 390, an image interpretation request to perform image interpretation on a part of the in-vivo image group that is cut out by the image cutting-out unit.

In this way, in the third embodiment of the present invention, it is possible to make an image interpretation request by cutting out a part of the in-vivo image in a group of in-vivo images while maintaining the ordering thereof in chronological order. Furthermore, for example, it is possible to embed, in the original group of in-vivo images, image interpretation operation data of a part of the in-vivo image that is requested outside for image interpretation operation and is obtained at the time of image interpretation while maintaining the ordering in chronological order. Accordingly, in the third embodiment of the present invention, it is possible to reduce the burden imposed on an in-house image interpreter at the time of image interpretation.

Modification 3-1

In the third embodiment described above, a case in which an image interpretation request is performed for the in-vivo image displayed in the main display area D13 has been described; however, the present invention is not limited thereto. A continuous multiple in-vivo images in a group of in-vivo images can also be requested to be subjected to image interpretation. In the following, such a case will be described in detail with reference to the drawings as modification 3-1 of the third embodiment of the present invention.

Figure 20:
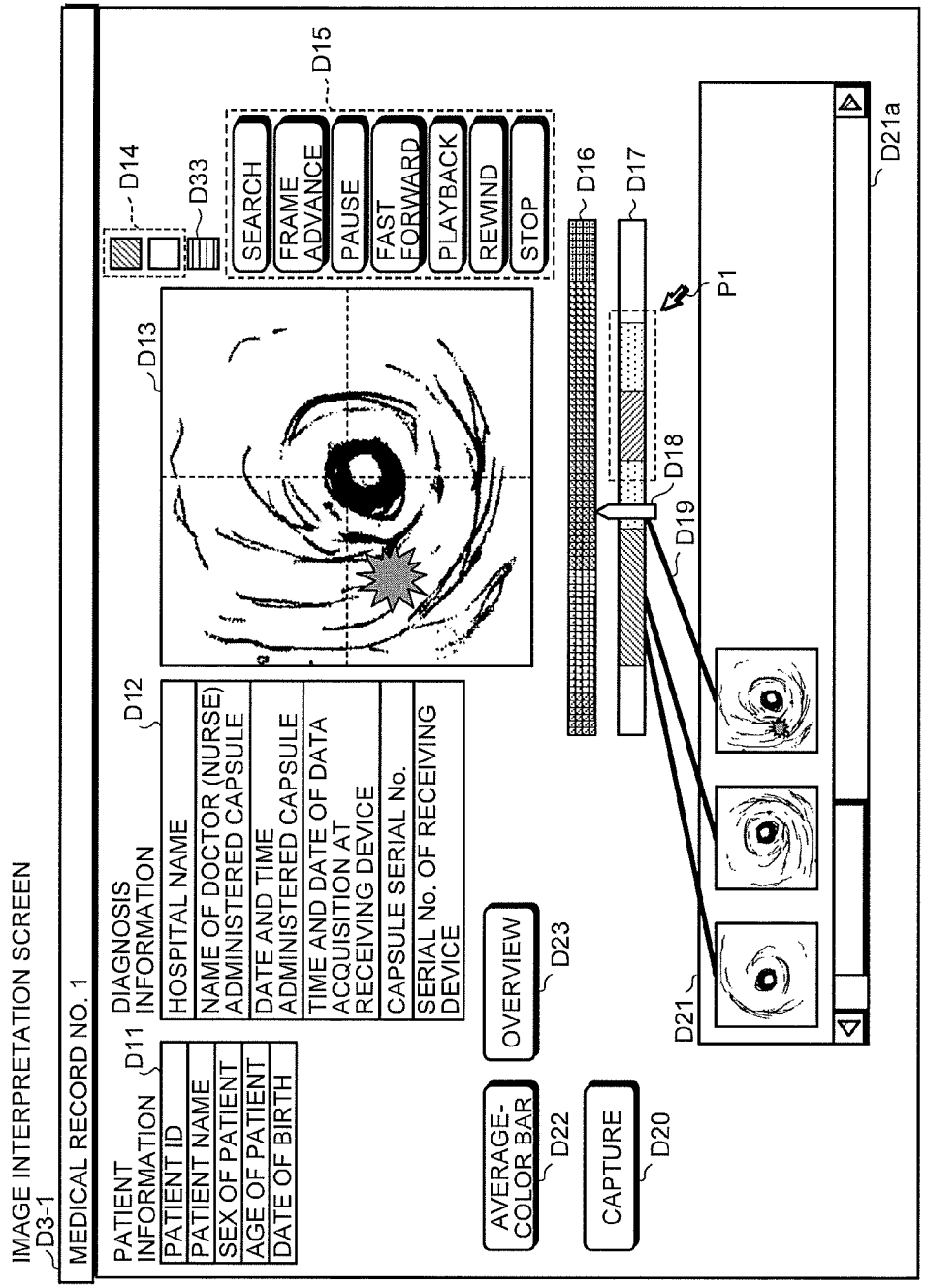
FIG. 20 is a schematic diagram illustrating an example of an image interpretation screen of an image display apparatus according to modification 3-1 of the third embodiment of the present invention.

FIG. 20 is a schematic diagram illustrating an example of an image interpretation screen D3-1 according to the modification 3-1 of the third embodiment of the present invention. As illustrated in FIG. 20, for example, if a user operates the pointer P1 using the operating unit 104 and drags an area in a certain region of the image interpretation process bar D17 on the image interpretation screen D3-1, the target interpretation image selection function 321 implemented by the control unit 101 selects one or more in-vivo images in this area as a target image for the image interpretation request. Subsequently, by executing the same operation as that performed by the request-source information processing unit 310 in the third embodiment described above, request data containing one or more in-vivo images that is selected as the target image for the image interpretation request is transmitted from the request-source information processing unit 310 to the request-destination information processing unit 380.

For example, it is preferable to use a different color or pattern for the region dragged and selected in the image interpretation screen D3-1 illustrated in FIG. 20 or for the region of the image interpretation process bar D17 associated with in-vivo images that are previously used for image interpretation requests. By doing so, a user can easily recognize which region of the in-vivo image is a target image for an image interpretation request or is previously used for an image interpretation request. Because the other configurations are the same as those in the embodiments or the modifications thereof described above, a description thereof in detail will be omitted here. It is possible to configure the request-source information processing unit 310 such that the target image for the image interpretation request is selected by dragging an area of a certain region of a simple time bar or the average-color bar D16 representing a time axis associated with a group of in-vivo images arranged in chronological order.

Modification 3-2

For example, if a group of in-vivo images is sectioned in association with an organ section, an image interpretation request can be performed for each organ section. In the following, such a case will be described in detail with reference to the drawings as modification 3-2 of the third embodiment of the present invention.

Figure 21:
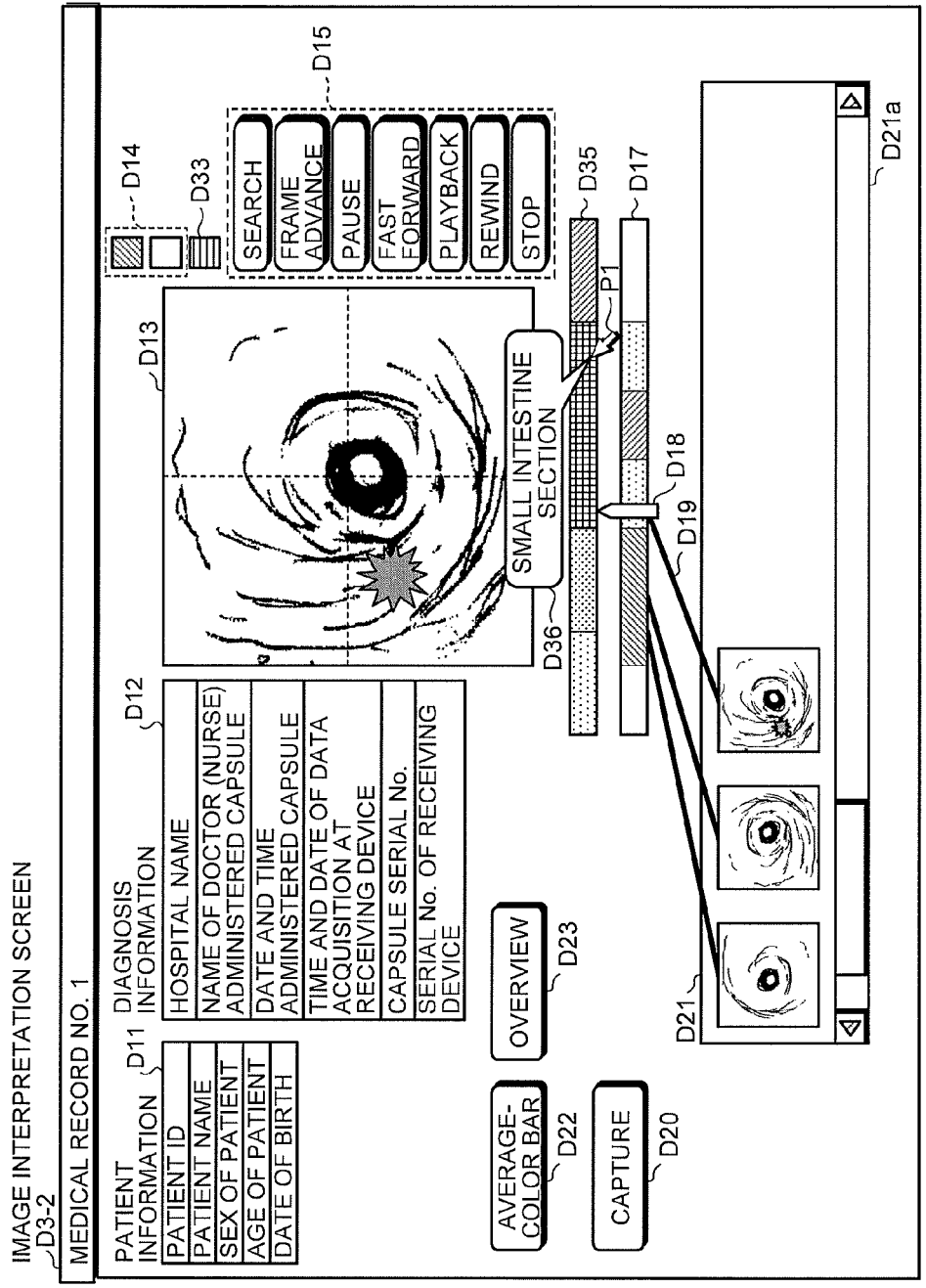
FIG. 21 is a schematic diagram illustrating an example of an image interpretation screen of an image display apparatus according to modification 3-2 of the third embodiment the present invention.

FIG. 21 is a schematic diagram illustrating an example of an image interpretation screen D3-2 according to the modification 3-2 of the third embodiment the present invention. As illustrated in FIG. 21, in the modification 3-2, instead of the average-color bar D16, an organ bar D35 is arranged vertically and in parallel with the image interpretation process bar D17. The organ bar D35 is color coded, for example, for each organ section. If a user moves the pointer P1 onto any one of the organ sections on the organ bar D35, for example, a message D36 according to the organ section is displayed in a pop-up window. If a user clicks the right mouse button in this state, the menu selection screen D31 similar to that in the third embodiment is displayed. In the subsequent processes, by performing the same processes as the image interpretation request in the third embodiment, it is possible to collectively perform image interpretation request with respect to in-vivo images for each organ section.

If the image interpretation request for each organ section is available in this way, a preferable configuration is one in which the organ sections are visually represented on, for example, the image interpretation process bar D17, the average-color bar D16, or a simple time bar, and a user can select a section used for the desired image interpretation request from that bar. Because the other configurations are the same as those in the embodiments or the modifications thereof described above, a description thereof in detail will be omitted here.

Modification 3-3

It is also possible to configure the request-source information processing unit so as to automatically extract an in-vivo image, such as an in-vivo image whose color is significantly different from that of the previous or subsequent image or extract an in-vivo image sectioned at the time of scene change and to allow a part or all of the in-vivo images to be collectively used for image interpretation requests. The degree of the color difference between previous and subsequent images can be calculated the brightness of red obtained when, for example, the average-color bar D16 is created. Furthermore, it is possible to specify the in-vivo image sectioned at the time of scene change using, for example, a scalar quantity of motion vector of the capsule endoscope 10 calculated from two, i.e., previous and subsequent, in-vivo images.

Modification 3-4

Figure 22:
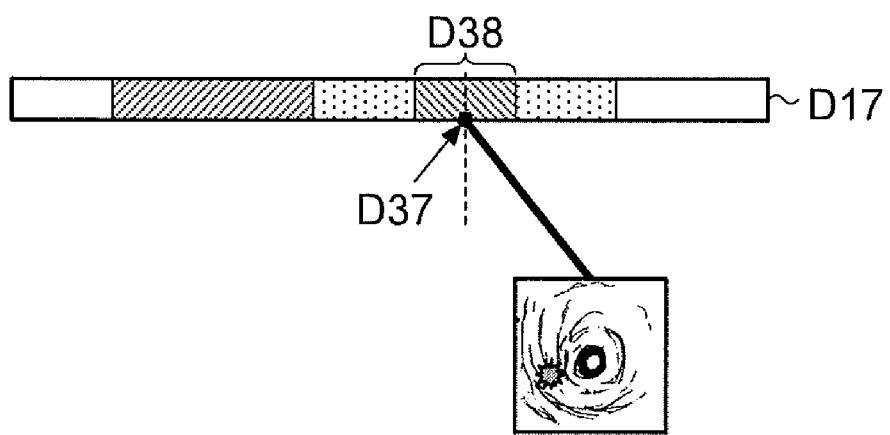
FIG. 22 is a schematic diagram illustrating a region of an image interpretation request performed by an image display apparatus according to modification 3-4 of the third embodiment of the present invention.

For example, if an observation is performed by capturing images of the same subject 900 for multiple times, it is also possible to configure the request-source information processing unit so as to automatically extract an in-vivo image of a portion that is not overlapped between different observations or extract an in-vivo image of an abnormality portion detected by image interpretation performed on a subject's image obtained in the previous observation and to allow that in-vivo image to be used for an image interpretation request. For example, as illustrated in FIG. 22, it is preferable to configure the request-source information processing unit such that an image interpretation request can also be collectively made for an in-vivo image corresponding to a region D38 having a certain rage including the position D37 that is on the image interpretation process bar D17 and that corresponds to the abnormality portion. FIG. 22 is a schematic diagram illustrating a region of an image interpretation request according to modification 3-4 of the third embodiment of the present invention. Because the other configurations are the same as those in the embodiments or the modifications thereof described above, a description thereof in detail will be omitted here.

Fourth Embodiment

In the following, the configuration and the operation of a capsule endoscope system and an image interpretation support system that include an image display apparatus according to a fourth embodiment of the present invention will be described in detail with reference to the drawings. In the fourth embodiment of the present invention, the capsule endoscope system 1 and the image interpretation support system 300 that are the same as those in the third embodiment described above are used as an example. In the following, components that are identical to those in the first, second, and third embodiments or the modifications thereof described FIG. 23 is a schematic diagram illustrating an example of an image interpretation screen D4-1 according to the fourth embodiment of the present invention. As illustrated in FIG. 23, on the image interpretation screen D4-1, an image interpretation request button D41 is added to a function similar to that of, for example, the image interpretation screen D1 in the first embodiment illustrated in FIG. 5. If a user operates the pointer P1 using the operating unit 104 and clicks the image interpretation request button D41, an image interpretation request screen D4-2 illustrated in FIG. 24 is displayed on the display unit 105.

FIG. 24 is a schematic diagram illustrating an example of the image interpretation request screen D4-2 according to the fourth embodiment of the present invention. As illustrated in FIG. 24, the followings are embedded in the image interpretation request screen D4-2: an image interpretation request list D42 that displays, as a list, an image interpretation request number that is an identification number of an image interpretation request registered as an assembly of at least one in-vivo image for the image interpretation request, displays a request destination that indicates each image interpretation request is requested to which request destination, and displays a reply due date that is the due date on which a reply is supposed to be received from each request destination; a display area D43 that displays a first in-vivo image or a representative image associated with each image interpretation request number; a request destination list D44 that indicates a request method of communicating or mailing for each request destination; an add button D45a, an edit button D45b, a delete button D45c, an output button D45d, and a transfer button D45e that are used to input an operation of adding, editing, deleting, outputting, and transferring an image interpretation request that is currently being selected in the image interpretation request list D42; an image interpretation process bar D17; a request area mark D47 that indicates that an in-vivo image corresponding to the image interpretation request in the image interpretation request list D42 corresponds to which position or area on the image interpretation process bar D17; and a slider D48 that indicates that an in-vivo image that is currently being displayed in the display area D43 corresponds to which position of the image interpretation process bar D17.

By operating the pointer P1, using the operating unit 104, on the image interpretation request screen D4-2, a user selects a target image interpretation request from the image interpretation request list D42. Furthermore, by operating the pointer P1 in a state in which the target image interpretation request is selected, a user selects, from the request destination list D44, a request destination to which the currently selected image interpretation request is made. Accordingly, the selected request destination is associated with the currently selected target image interpretation request.

As described above, after at least one pair of image interpretation request and request destination is associated, if a user operates the pointer P1 and clicks the transfer button D45e, request data of an image interpretation request that is associated with a request destination and that has not been made is transmitted to the request destination. If the output button D45d is clicked instead of the transfer button D45e, the request data of the currently selected target image interpretation request is stored in a recording medium, such as a DVD-RAM, for each request destination.

As described above, if an image interpretation request is made, a request date is recorded in the image interpretation request progress information storing unit 102h in the memory unit 102 in such a manner that the request date is associated with an image interpretation request number and information on a request destination. Furthermore, the image interpretation request list D42 on the image interpretation request screen D4-2 is updated to the latest information. Furthermore, for a requested image interpretation request, i.e., an image interpretation request that has been transmitted or output, a mark, such as a check-mark, is added thereto in association with, for example, a request destination.

Furthermore, by using the request date and the request destination of the image interpretation request, the image interpretation request management function 324 in the control unit 101 automatically specifies a reply due date and records it in the image interpretation request progress information storing unit 102h. The image interpretation request list D42 on the image interpretation request screen D4-2 is updated to the latest information. However, the reply due date can also be manually registered.

Furthermore, by changing a color or a pattern of the image interpretation process bar D17 in accordance with progress information on image interpretation, such as unrequested, requested, an undelivered reply, or a delivered reply, a user easily and visually recognizes the status of the image interpretation of an in-vivo image in each region.

Because the other configurations and operations are the same as those in the embodiments or the modifications thereof described above, a description thereof in detail will be omitted here.

The embodiments as described above are just examples of the present invention and thus do not limit the invention. It should be obvious that the above description could make the various changes according to specifications and the like within the scope of the invention and other various embodiments within the scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus comprising:
an image playback unit that plays a group of a series of images arranged in chronological order;
an operating unit that is used to input an operation when an image that is being played in the image playback unit is subjected to image interpretation;
an image interpretation operation recording unit that records an operation content that are input from the operating unit in an order with respect to the image that is being played in the image playback unit;
an image interpretation operation image creating unit that creates, using the operation content recorded in the image interpretation operation recording unit, a series of images according to the order; and
an image interpretation operation image display unit that displays the images created by the image interpretation operation image creating unit.

2. The image display apparatus according to claim 1, wherein
the image interpretation operation recording unit records the operation content for each of different image interpretation operations,
the image interpretation operation image creating unit creates images for each of the image interpretation operations by using one or a plurality of operation contents for each of the image interpretation operations, and the image interpretation operation image display unit displays the images for each of the image interpretation operations.

3. The image display apparatus according to claim 2, wherein the image interpretation operation image display unit displays the images for each of the image interpretation operations while associating the order among the images for each of the image interpretation operations.

4. The image display apparatus according to claim 2, wherein the image interpretation operation image creating unit creates the images for each of the image interpretation operations using a different color or pattern for each of the image interpretation operations.

5. The image display apparatus according to claim 1, further comprising:

an average value calculating unit that calculates an average value of operation contents that are recorded for each of different image interpretation operations in the image interpretation operation recording unit, wherein the image interpretation operation image creating unit creates the images using the average value calculated by the average value calculating unit.

6. The image display apparatus according to claim 1, wherein the image interpretation operation image creating unit updates the images from an image interpretation operation that is currently in progress performed on the group of the series of images and using the operation content recorded by the image interpretation operation recording unit, and the image interpretation operation image display unit updates an image that is being displayed using the images updated by the image interpretation operation image creating unit.

7. The image display apparatus according to claim 1, wherein the image interpretation operation recording unit records a plurality of operation contents having different contents with respect to a same image interpretation operation, the image interpretation operation image creating unit creates, using one or a plurality of operation contents having different contents, images for each of the operation contents having different contents, and the image interpretation operation image display unit displays the images for each of the operation contents having different contents.

8. The image display apparatus according to claim 7, wherein the image interpretation operation image display unit displays the images for each of the operation contents having different contents while associating the order with the images for each of the operation contents having different contents.

9. The image display apparatus according to claim 7, wherein the image interpretation operation image creating unit creates the images for each of the operation contents having different contents using a different color or pattern for each of the operation contents having different contents.

10. The image display apparatus according to claim 1, further comprising:

a priority adding unit that adds priority for each of the operation content, wherein the image interpretation operation image creating unit creates the images using an operation content that has the highest priority.

11. The image display apparatus according to claim 10, wherein the image interpretation operation image display unit displays the images for each of the operation content while aligning the images for each of the operation content in order of the priority.

12. The image display apparatus according to claim 1, wherein the group of the series of images is a group of in-vivo images obtained by periodically capturing inside a subject.

13. The image display apparatus according to claim 1, wherein the operation content includes at least one of a display time and/or the number of display times for each image of the group of the series of images, a support function that is used when each image is subjected to image interpretation, and a capture history of each image.

14. The image display apparatus according to claim 1, further comprising:

an image cutting-out unit that cuts out a part of the group of the series of images in the order; and an image interpretation request transmitting unit that transmits, to a request destination via a network, an image interpretation request of the part of the group that is cut out by the image cutting-out unit.

15. The image display apparatus according to claim 14, wherein the image interpretation request transmitting unit transmits the part of the group to a plurality of request destinations via the network.

16. An image interpretation support system comprising:

an image display apparatus comprising:

an image playback unit that plays a group of a series of images arranged in chronological order;

an operating unit that is used to input an operation when an image that is being played in the image playback unit is subjected to image interpretation;

an image interpretation operation recording unit that records an operation content that are input from the operating unit in an order with respect to the image that is being played in the image playback unit;

an image interpretation operation image creating unit that creates, using the operation content recorded in the image interpretation operation recording unit, a series of images according to the order;

an image interpretation operation image display unit that displays the images created by the image interpretation operation image creating unit;

an image cutting-out unit that cuts out a part of the group of the series of images in the order; and an image interpretation request transmitting unit that transmits, to a request destination via a network, an image interpretation request of the part of the group that is cut out by the image cutting-out unit; and a request-destination information processing unit that receives the image interpretation request from the image display apparatus.

17. A non-transitory computer-readable recording medium storing an image interpretation support program for operating an image display apparatus that supports image interpretation of a group of a series of images arranged in chronological order, the image interpretation support program causing the image display apparatus to execute:

an image play process of playing the group of the series of images;

an image interpretation monitoring process of monitoring an operation that is input when an image that is being played is subjected to image interpretation;

an image interpretation operation recording process of recording an operation content in an order, obtained at the image interpretation operation recording process with respect to the image that is being played;

an image interpretation operation image creating process of creating a series of images in accordance with the order using the operation content recorded at the image interpretation operation recording process; and an image interpretation operation image display process of displaying the image created at the image interpretation operation image creating process.

18. The image display apparatus according to claim 1, wherein the image interpretation operation image creating unit creates the series of images indicating a process of the image interpretation currently or previously performed on the group of the series of images, according to the chronological order.

* * * * *